(12) United States Patent
Itescu

(10) Patent No.: US 7,135,302 B1
(45) Date of Patent: Nov. 14, 2006

(54) METHOD FOR PREDICTING TRANSPLANT REJECTION

(76) Inventor: Silviu Itescu, 279 E. 44th St., Apt. 12E, New York, NY (US) 10017

(*) Notice: Subject to any disclaimer, the term of this patent is extended or adjusted under 35 U.S.C. 154(b) by 0 days.

(21) Appl. No.: 09/509,734

(22) PCT Filed: Oct. 2, 1998

(86) PCT No.: PCT/US98/20887

§ 371 (c)(1),
(2), (4) Date: Jun. 14, 2000

(87) PCT Pub. No.: WO99/18231

PCT Pub. Date: Apr. 15, 1999

Related U.S. Application Data

(60) Provisional application No. 60/090,153, filed on Jun. 22, 1998, provisional application No. 60/060,992, filed on Oct. 3, 1997.

(51) Int. Cl.
 *C12Q 1/68* (2006.01)
 *G01N 33/53* (2006.01)

(52) U.S. Cl. ................... 435/7.24; 435/6; 435/91.2; 435/91.21

(58) Field of Classification Search ............ 435/6, 435/7.24, 91.2, 91.21
See application file for complete search history.

(56) References Cited

OTHER PUBLICATIONS

Itescu et al, Circulation, 98(8), 786-793, 1998.*
Lazada, Transplantation, 57(6), 964-969, 1994.*
Ten Hoor et al, Transplantation, 56(2), 298-304, 1993.*
Hosenpud J.F., Novick R.J., Bennett L.E., Keck B.M., Fiol B., Daily P.O. The Registry of the International Society of Heart and Lung Transplantation 1996; 15:655.
Kormos, R., Arimtage, J., Wolyn, T. et al. Graft atherosclerosis: effects of cellular rejection and human lymphocyte antigen. The Journal of Heart and Lung Transplantation 1992; 11(3):S104-110.
Kerman, R.H., Kimball, P., Scheinen, S. et al. The relationship among donor-recipient HLA mismatches, rejection, and death from coronary artery disease in cardiac transplant recipients. Transplantation 1994; 57(6); 884-8.
Smith, J.D., Rose, M.L., Pomerance, A., Burke, M., Yacoub, M.H. Reduction of cellular rejection and increase in longer-term survival after heart transplantation after HLA-DR matching. Lancet 1995; 346:1318-22.
Costanzo-Nordin, M.R. Cardiac allograft vasculopathy: relationship with acute cellular rejection and histocompatibility. The Journal of Heart and Lung Transplantation 1992; 11:S90-103.
Suciu-Foca N., Reed E., Marboe C., Xi Y.P., Kai S.Y., Ho E., Rose E.A., Reemstma K., King, D.W. Role of anti-HLA antibodies in heart transplantation. Transplantation 1991; 51:716-724.

(Continued)

*Primary Examiner*—David Saunders
(74) *Attorney, Agent, or Firm*—Baker Botts LLP

(57) ABSTRACT

The present invention relates to a method for predicting whether or not transplant recipients are likely to reject tissue allografts. It is based, at least in part, on the discovery that, based on analysis of three immunologic factors, cardiac transplant recipients could be classified into risk categories for progression to high-grade rejection. The present invention, by enabling a determination of the risk for high-risk rejection in a transplant patient, reduces unnecessary diagnostic and therapeutic procedures in low risk patients and clinical intervention in patients who would most benefit.

8 Claims, 8 Drawing Sheets

OTHER PUBLICATIONS

Figure 1:
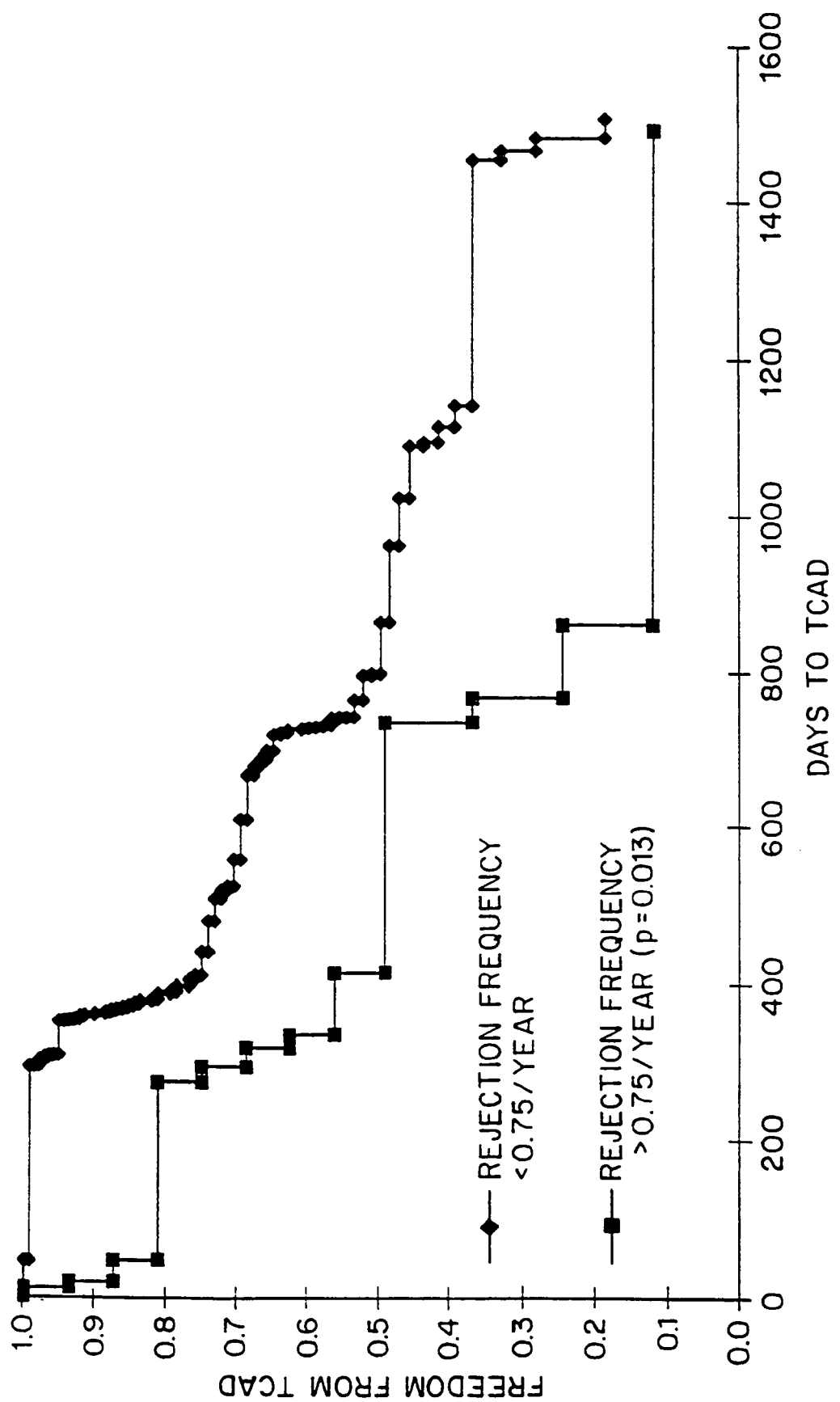

Hess M., Hastillo A., Mohanakamar T., Crowley J.J., Vetrovac G., Szentpetery, S., Wolfgang, T.C., Lower R.R.. Accelerated atherosclerosis in cardiac transplantation: role of cytoxic B-cell antibodies and hyperlipidemia. Circulation 1983; 68:94-101.

Rose, E.A., Pepino P., Barr M., Smith C., Ratner A., Ho E., Berger C. Relation of HLA antibodies and graft atherosclerosis in human cardiac allograft recipients. The Journal of Heart and Lung Transplantation 1992; S120-123.

DeMattos, A.M. Head M.A., Everett, J., et al. HLA-DR mismatching correlates with early cadiac allograft rejection, incidence, and graft survival when high-confidence-level serological DR typing is used. Transplantation 1994; 57(4);626-630.

Kriklin, J.K., Bourge, R.C., BBarr, M.L., et al. Influence of HLA mismatch on rejection after heart transplantation: a multiinstitutional study. The cardiac transplant research databae group. The Journal of Heart and Lung Transplantation. 1995; 13(4); 583-95.

Keogh, A., Kaan, A., Doran, T., et al. HLA mismatching and outcome in heart, heart-lung and single lung transplantation. The Journal of Heart and Lung Transplantation. 1995; 14(3);444-51.

Fischer, P.E., Suciu-Foca, N., Ho, E., Tugulea, S., Rose E.A., Michler, R.E., Mancini, D. Additive value of immunologic monitoring to histologic grading of heart allograft biopsy speciments: implications for therapy. Journal of Heart and Lung Transplantation 1995; 14:1156-1161.

Liu, Z., Sun, Y.K., Xi, Y.P., Maffei, A., Harris, P.E., Suciu-Foca, N. Contribution of direct and indirect recognition pathway to T cell alloreactivity. Journal of Experimental Medicine 1993; 177:1643-1650.

Liu, Z., Colovai, A.I., Tugulea, S., Reed, E.F., Fisher, P.E., Mancini, D., Rose, E.A., Cortesini, R., Michler, R.E., Suciu-Foca, N., Indirect Recognition of donor HLA-DR peptides in organ allograft rejection. Journal of Clinical Investigation 1996; 98:1150-1157.

Tugulea, S., Ciubotariu, R., Colovai, A.I., Liu, Z., Itescu, S., Schulman, L., Fisher, P.E., Hardy, M.A., Rose, E.A., Michler, R.E., Cortesini, R., Suciu-Foca, N. New strategies for early diagnosis of heart allograft rejection. Transplantation 1997: 64:842-847.

Ciubotariu, R., Colovai, A.I., Ho, E., Itescu, S., Ravalli, S., Hardy, M.A., Cortesini, R., Rose, E.A., Suciu-Foca, N. Persistant allopeptide reactivity and epitope spreading in chronic rejection of organ allografts. Journal of Clinical Investigation 1998; 101:398-405.

Markus, P.M., Salvaggi, G., Cai, X., Fung, J.J., Starzl, T.E. Induction of donor-specific transplantation tolerance ot skin and cardiac allografts using miched chimerism in (A+B ->A) in rats. Cell Transplantation 1993; 2:345-353.

Zeevi, A., Pavlick, M., Lombardozzi, S., Banas, R., Pappo, O., Rao, A.S., Fontes, P., Demetris, J., Shapiro, R., Dodson, E., et al. Immune status of recipients following bone marrow-augmented solid organ transplantation. Transplantation 1995; 59:616:620.

Creemers, P. Du Toit, E., Cassidy, M.J., Kahn, D. Sequential mixed lymphocyte culture after kidney transplantation: induction of tolerance or sensitization. Nephron 1997; 75: 166-170.

Billingham, M.E. Dilemma of variety of histopathologic grading systems for acute cardiac allograft rejection by endomyocardial biopsy. Journal of Heart Transplantation 1990; 9:272-276.

Kaplan, E.L., and Meier, P. Nonparametric estimation from incomplete observations. Journal of the American Statistic Association 1958; 53: 457-481.

Liang, K.Y., and Zenger, S.L. Longitudinal data analysis using generalized linear models. Biometrica 1986; 73: 13-22.

Krieger, N.R., Yin, D.P., and Fathman, C.G. CD4+ but not CD8+ cells are essential for allorejection. Journal of Experimental Medicine 1996; 84:2013-2018.

Starzl, T.E., Demetris, A.J., Rao, A.S., Thompson, A.M., Trucco, M., Murase, N. Migratory nonparenchymal cells after organ allotransplantation: with particular reference to chimerism and the liver. Progress in Liver Diseases 1994; 12:191-213.

Schlitt, H.J., Hundrieser, J., Hisanaga, M., Uthoff, K., Karck, M., Wahlers, T., Wonigeit, K., Pichlmayr, R. Patterns of donor type microchimerism after heart transplantation. Lancet 1994; 343:1469-1471.

Hisanaga, M., Hundrieser, J., Boker, K., Uthoff, K., Raddaatz, G., Wahlers, T., Winigeit, K., Pichlmayr, R., Schlitt, H.J. Development, stability, and clinical correlations of allogeneic microchimerism after solid organ transplantation. Transplantation 1996: 61:40-45.

Vanderlugt, C.J. and Miller, S.D., Epitope spreading. Current Opinion in Immunology 1996; 8:831-836.

Mamula, M.J. and Janeway, C.A. Jr. Do B cells drive the diversification of immune responses? Immunology Today 1993; 14:151-154.

Reed, E.F., Hong, B., Ho, E., Harris, P.E., Weinberger, J., Suciu-Foca, N. Monitoring of soluble HLA alloantigens and anti-HLA antibodies identifies heart allograft recipients at risk of transplant associated coronary artery disease. Transplantation 1996; (61)566-72.

Itescu, S., Weinberg, A., Burke, E.M., Tung, T., Oz, M., Reed, E., Suciu-Foca, N., Rose, E.A., Michler, P.E. Influence of pre-formed IgG anti-HLA antibodies on development of cellular rejection in highly sensitized cardiac allograft recipients. The Journal of Heart and Lung Transplantation 1997: 16(1): 78.

Lavee, J., Kormos, R.L., Duquesnoy, R.J., Zerbe, T.R., Armitage, J.M., Vaneck, B.S., Hardesty, R.L., and Griffith, B.P. Influence of panel-reactive antibody and lymphocytotoxic crossmatch on survival after heart transplantation. Journal of Heart and Lung Transplantation 1991; 6:921-930.

Loh, E., Bergin, J.D., Couper, G.S., Mudge, G.H. Role of panel-reactive antibody cross-reactivity in predicting survival after orthotopic heart transplantation. Journal of Heart and Lung Transplantation 1994; 13:194-201.

Valentine, H.A., Yeoh, T.K., Gibbons, R., McCarthy, P., Stinson, E.B., Billingham. M.E., Popp, R.L. Sensitivity and specificity of diastolic indexes for rejection surveillance: temporal correlation with endomyocardial biopsy. Journal of Heart and Lung Transplantation 1991; 10:757-765.

Tugulea et al., 1997, "New Stategies for Early Diagnosis of Heart Allograft Rejection," Transplantation (Williams and Wilkins, Baltimore, MD, US) 64(6):842-847.

Jutte et al., 1994, "The Development of Transplant Coronary Artery Disease After Cardiac Transplantation is Correlated with a Predominance of CD8+ T Lymphocytes in Endomyocardial Biopsy Derived T Cell Cultures," Clinical and Experimental Immunology 98(1):158-162.

Panajotopoulos et al., 1992, "A Successful Second Renal Allograft Across Positive B-Cell Crossmatch due to IgG Anti-HLA DR5 Antibody," Clinical Transplantation (Munksgaard, Copenhagen, DK) 6(3I):196-198.

Taylor et al., 1987, "A Positive B Cell Crossmatch due to IgG Anti-HL:A Antibody Present at the Time of Transplantation in a Successful Renal Allogaft," Tissue Antigens 30(3):104-112.

Rizeq, M., Masek, M.A., and Billingham, M.E. Acute rejection: significance of elapsed time after transplantation. The Journal of Heart and Lung Transplantation. 1994; 13(5); 862-868.

Winters, G.L., Loh, E., Schoen, F.J., Natural history of focal moderate cardiac allograft rejection: is treatment warranted. Circulation. 1995:91:1975-1980.

White J.A., Guirandon C., Pfluglelder P.W., Kostuk W.J. Routine surveillance myocardial biopsies are unnecessary beyond one year after heart transplantation. The Journal of Heart and Lung Transplantation 1995; 14:1052.

Smith, J.D., Danskine, A.J., Laylor, R.M., Rose, M.L., and Yacoub, M.H. THe effect of panel reactive antibodies and the donor specific corssmatch on graft survival after heart and heart-lung transplantation. Transplant Immunology 1993; 1:60-65.

Rose, E.A., Smith, C.R., Petrossian, G.A., Barr, M.L., Reemtsma, K. Humoral Immune responses after cardiac transplantation: correlation with fatal rejection and graft atherosclerosis. Surgery 1989; 106:203-208.

Kernkes, B.M., Schultz, A., Engelhardt, M., Brandl, U., and Breuer, M. Noninvasive methods of rejection diagnosis after heart transplantation. The Journal of Heart and Lung Transplantation 1992; 11:S221-S231.

Hall T., Baumgartner W., Borkin A., et al. Diagnosis of acute cardiac rejection with antimyosin antibody monoclonal antibody, phosphorus nuclear magnetic imaging, two dimensional echocardiography and endocardial biopsy. The Journal of Heart Transplantation 1986; 6:419-24.

Wisenberg G., Pflugfelder J.V., Kostuk, W.J., McKenzie F.N., Prato F.S. Diagnostic applicability of magnetic resonance imaging in assessing human cardiac allograft rejection. American Journal of Cardiology 1987; 53:130.

George, J.F., Kirklin, J.K., Shroyer, T.W., et al. Utility of a post-transplantation panel-reactive antibody measurements for the prediction of rejection frequency and survival or heart transplant recipients. The Journal of Heart and Lung Transplantation 1995; 14:856-864.

Smith, J.D., Danskine, A.J., Rose, M.L., and Yacoub, M.K. Specificity of lymphocytotoxic antibodies formed after cardiac transplantation and correlation with rejection episodes. Transplantation 1992; 53:1358-62.

Zavazava, N., Botcher, H., and Ruchholtz, W.M., Soluble MHC Class I antigens (sHLA) and anti-HLA antibodies in heart and kidney allograft recipients. Tissue Antigens 1993; 42:20-26.

* cited by examiner

METHOD FOR PREDICTING TRANSPLANT REJECTION

This application claims priority to PCT/US98/20887 filed Oct. 2, 1998 which claims priority to provisional application 60/090,153 filed Jun. 22, 1998 and provisional application 60/060,992 filed Oct. 3, 1997.

1. INTRODUCTION

The present invention relates to a method for predicting whether or not transplant recipients are likely to reject tissue allografts. It is based, at least in part, on the discovery that, based on analysis of three immunologic factors, cardiac transplant recipients could be classified into risk categories for progression to high-grade rejection. The present invention, by enabling a determination of the risk for high-risk rejection in a transplant patient, reduces unnecessary diagnostic and therapeutic procedures in low risk patients and clinical intervention in patients who would most benefit.

2. BACKGROUND OF THE INVENTION

The long-term success of cardiac transplantation is currently limited by the high incidence of transplant-related coronary artery disease (TCAD) (Hosenpud et al., 1996, J. Heart and Lung Transplantation 15:655). This complication may be related to the recipient's ongoing immune response against donor major histocompatibility complex (MHC) antigens since long-term allograft survival correlates directly with the number of donor-recipient human leukocyte antigen (HLA) matches (Kormos, et al., 1992, J. Heart and Lung Transplantation 11(3:S104–110; Kerman, et al., 1994, Transplantation 1994, 57(6): 884–8); Smith, et al., 1995, Lancet 346: 1318–22; Constanzo-Nordin, M. R., 1992, J. Heart and Lung Transplantation 11: S90–103) and inversely with the development of circulating antibodies against donor HLA molecules (Suciu-Foca, et al., 1991, Transplantation 51:716–724; Hess, et al., 1983, Circulation 68:94–101; Rose, et al., 1992, J. Heart and Lung Transplantation S120–123). Moreover, since donor/recipient HLA-DR mismatching is associated with increased cardiac allograft rejection episodes (DeMattos, et al., 1994, Transplantation 57(4)626–630; Kirklin, et al., 1994, Transplantation 13(4): 583–95; Keogh, et al., 1995, J. Heart and Lung Transplantation 14(3):444–51), TCAD may be the end result of recurrent or persistent allograft rejection (Constanzo-Nording, M. R., 1992, J. Heart and Lung Transplantation 11: S90–103).

In order to identify patients at high risk of having a positive donor-specific cross-match, cardiac transplantation candidates are prospectively tested for anti-HLA antibodies against lymphocytes from a panel of volunteers representative of the major HLA allotypes, collectively referred to as measurements of panel-reactive antibodies (PRA). In addition to predicting an increased likelihood of donor-specific anti-HLA antibodies and a consequent risk of early graft failure related to humoral rejection, several studies have shown that high levels of pretransplant PRA in cardiac allograft recipients are associated with adverse post-transplant outcome when compared to patients with low or negative reactivity (Smith et al., 1993, Transplant Immunol. 1:60–65). High PRA levels have been associated, in some studies, with increased frequency of acute cellular rejections, decreased long-term graft survival, and increased mortality (Lavee et al., 1991, J. Heart and Lung Transplantation 10:921–930; Loh et al., 1994, J. Heart and Lung Transplantation 13:194–201). Moreover, the onset of accelerated coronary artery disease (CAD) in cardiac transplant recipients, the major limitation to long-term graft survival, has been associated with the presence of anti-HLA antibodies (Hess et al., 1983, Circulation 68:94–101; Rose et al., 1989, Surgery 106:203–208; Suciu-Foca et al., 1991, Transplantation 51:716–724). Since accelerated CAD in these patients may be a consequence of cumulative episodes of high-grade cellular rejections, it is possible that this association may actually reflect a relationship between anti-HLA antibodies and acute cellular rejection.

The only consistently reliable method for diagnosis of cardiac allograft rejection in patients who have received a transplant is the endomyocardial biopsy (EMB). The probability of progression from a negative or low-grade EMB to a high-grade biopsy is greatest during the first six months following transplantation (Rizeq, et al., 1994, J. Heart and Lung Transplantation 13(5):862–868; Winters, et al., 1995, Circulation 91:1975–1980; White, et al., 1995, J. Heart and Lung Transplantation 14:1052; Billingham, M., 1990, J. of Heart and Lung Transplantation 9:77). Since the EMB can only diagnose established rejection episodes, and the procedure has several drawbacks, including risk of complications, high cost, sampling error, and potential variation in interpretation, it would be highly desirable to have non-invasive modalities to prospectively identify patients at high risk of progression from a low to high EMB grade. Although various non-immunologic modalities, including measurement of hemodynamic parameters (Valentine, et al., 1991, J. Heart and Lung Transplantation 10:557), radionuclide scanning (Kemkes, et al. 1992, J. Heart and Lung Transplantation 10:557), and magnetic resonance imaging (Baumgartner, 1986, J. Heart and Lung Transplantation 5:419; Wisenberg, 1987, American Journal of Cardiology, 60:130), have shown good correlation with established high-grade rejections, none have demonstrated sufficient predictive value to be included in routine clinical management. Among immunologic assays, measurement of panel-reactive anti-HLA antibodies (George, et al., 1995, J. Heart and Lung Transplantation 14:856–864; Smith, et al., 1992, Transplantation 53:1358–62; Zavazava, et al., 1993, Tissue Antigens 42:20–26), detection of IL-2 activated T cells in the allograft using a 48-hour IL-2 dependent lymphocyte growth assay (LGA) (Fischer, et al., 1995, J. Heart and Lung Transplantation 14:1156–1161), recipient sensitization to donor derived HLA peptides (Liu, et al., 1993, J. Experimental Medicine 177:1643–1650), (Liu, et al., 1996, J. Clinical Investigation 98:1150–1157; Tugulea, et al., 1997, Transplantation 64:842–847; Ciubotariu, 1998, J. Clinical Investigation 101:398–405), and lack of induction of donor-specific hyporeactivity, as measured by recipient T cell proliferation against donor cells (Markus, et al., 1993, Cell Transplantation 2:345–353; Zeevi, et al., 1995, Transplantation 59:616–620; Creemers, et al., 1997, Nephron 75:166–170) have been shown to correlate with episodes of established cellular rejection, however the predictive value of these assays has not been extensively evaluated.

Currently, five year allograft survival is estimated to occur in 70% of cardiac transplantation patients; with approximately 40% of patients experience a high-grade rejection episode in the first year after transplant. For transplants involving other tissues, long-term graft survival continues to be a problem. For example, in kidney and liver the ten year survival rate is approximately 50%; for lung and pancreas the three year survival rate is approximately 50%.

The immunological basis for transplant rejection is the subject of extensive research. Cumulative experimental data in rodent models suggest that initiation of allograft rejection is predominantly a CD4 T cell-dependent process, and that there may not be an absolute requirement for CD8 cells (Krieger, et al., 1996, J. Experimental Medicine 184:2013–2018). Moreover, long-term graft acceptance appears to be associated with reduced direct recognition of donor alloantigens by recipient CD4 T cells (Zeevi, et al., 1995, Transplantation 59:616–620; Creemers, et al., 1997, Nephron 75:166–170). Donor-specific hyporesponsiveness can be augmented by infusion of donor bone marrow cells at the time transplantation (Zeevi, et al., 1995, Transplantation 59:616–620), and may be accompanied by persistent microchimerism (Starzl, et al., 1994, Progress in Liver Diseases 12:191–123), suggesting that recipient CD4 T cells can be rendered tolerant to direct allostimulation by donor leukocytes. However, since donor-type microchimerism has not been found to correlate well with either acute or chronic allograft rejection (Schlitt, et al., 1994, Lancet 343:1469–1471), mechanisms other than direct allorecognition may significantly impact on allograft rejection. Recent evidence has emerged that over time the indirect pathway of CD4 T cell activation plays an increasingly important role in the development of acute and chronic allograft rejection (Liu, et al., 1993, J. Experimental Medicine 177:1643–1650). This may be a consequence of continuous shedding of donor alloantigenic HLA peptides and their processing by host antigen-presenting cells (APCs) such as macrophages and B cells. Primary rejections appear to be invariably accompanied by recipient T cell recognition of a dominant HLA-DR allopeptide presented by self-APCs (Liu, et al., 1996, J. Clinical Investigation 98:1150–1157; Tugulea, et al., 1997, Transplantation 64:842–847), whereas recurrent rejections, as well as the onset of TCAD, appear to be accompanied by inter- and intra-molecular spreading and T cell recognition of multiple donor HLA-DR alloantigenic determinants (Tugulea, et al., 1997, Transplantation 64:842–847; Ciubotariu, 1998, J. Clinical Investigation 101: 398–405). This diversification of the immune response has been postulated to be a result of activation of antigen-specifics B cells by soluble MHC class II products, particularly HLA-DR molecules, and the subsequent efficient presentation of multiple HLA-DR allopeptides by self B cells to CD4 T cells (Vanderlugt, et al., 1996, Current Opinion in Immunology 8:831–836; Mamula, et al., 1993, Immunology Today 14:151–154; Reed, et al., 1996, Transplantation 61:556–572).

3. SUMMARY OF THE INVENTION

The present invention relates to a method for determining that a subject is at risk for developing a high-grade rejection of a tissue transplant based on the presence or absence of at least one HLA-DR match, and on the results of two particular assays, namely the lymphocyte growth assay and an assay to determine the presence, in the subject, of IgG anti-MHC Class II antibodies. A subject who is determined to be at low risk for high grade rejection may be allowed to experience an interval without additional clinical intervention, for a reasonable period of time. A subject determined to be at moderate risk may be subjected to further and/or more frequent diagnostic procedures. A subject determined to be at high risk may be aggressively treated so as to avoid the occurrence of a high-grade rejection episode.

Although the comparison of the major histocompatibility antigens HLA-DR, the detection of IgG directed toward MHC Class II antigens, and the lymphocyte growth assay have been known in the art, it had not, prior to the invention, been known that combining these three variables would result in a means to identify high-risk transplant recipients with a predictive value exceeding 80 percent.

The present invention, by enabling a determination of the risk for high-risk rejection in a transplant patient, reduces unnecessary diagnostic and therapeutic procedures in low risk patients, and directs clinical intervention toward those patients who will most benefit. For example, in the specific, nonlimiting embodiment of the invention involving cardiac transplantation, for individuals whose immunologic profiles indicate a persistently low risk for high grade rejection, the invention has the potential to significantly reduce the number of endomyocardial biopsies being performed during the first year.

Secondly, the prospective identification of patients at high risk for grade 3A rejections will enable rational institution of interventional therapy to reduce anti-donor alloreactivity and prevent high-grade rejection episodes. Since adequate reversal of already established high-grade rejections does not prevent the subsequent sequelae of transplant-related coronary artery disease, only by preventing high-grade rejections from occurring can the incidence of this principal complication be reduced and/or its onset delayed.

In addition, the present invention relates to the determination that a subject is likely to experience a rejection episode either pre- or post transplant, based on the presence of IgG anti-MHC Class II antibodies. Prior to the invention, the particular significance of the presence of detectable IgG antibodies directed at MHC Class II, as opposed to Class I, antigens had not been appreciated.

4. DESCRIPTION OF THE FIGURES

FIG. 1. Kaplan-Meier time-dependent analysis of onset of transplant-related coronary artery disease (TCAD) in patients stratified into four groups by increasing cumulative annual rejection frequency (<0.25/yr, 0.25–0.5/yr., 0.5–0.75/yr, >0.75/yr). A threshold of greater than 0.75 high-grade rejections per year was associated with a significantly shorter time to developing TCAD (p=0.0002).

Figure 2:
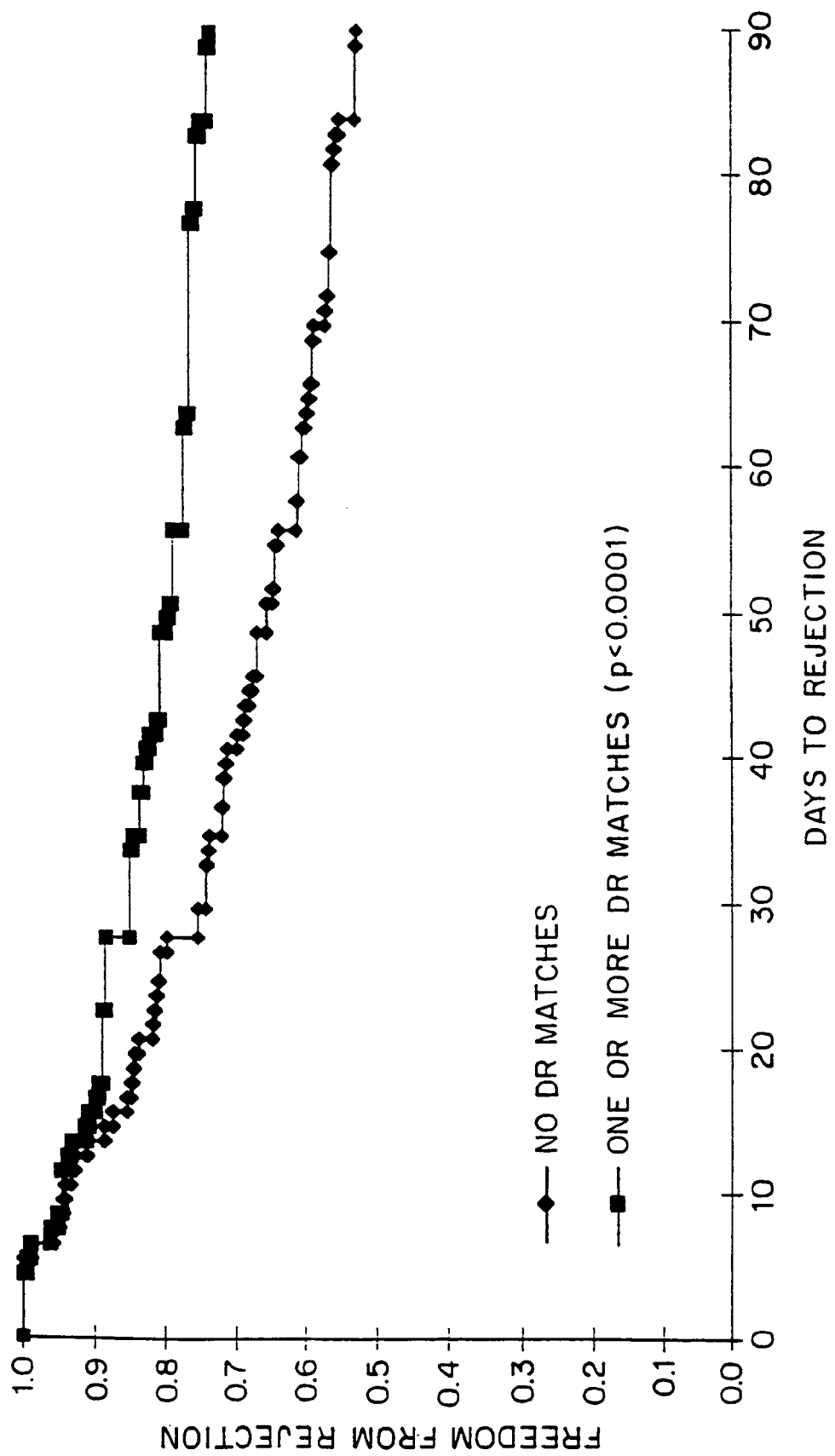

FIG. 2. Influence of matching at the HLA-DR locus on progression to a high-grade rejection within 90 days of having a low-grade EMB during the first year post cardiac transplantation. One or more matches between recipient and donor at the HLA-DR locus protects cardiac allograft recipients from developing high-grade rejections (odds ratio 2.42, p<0.0001).

Figure 3:
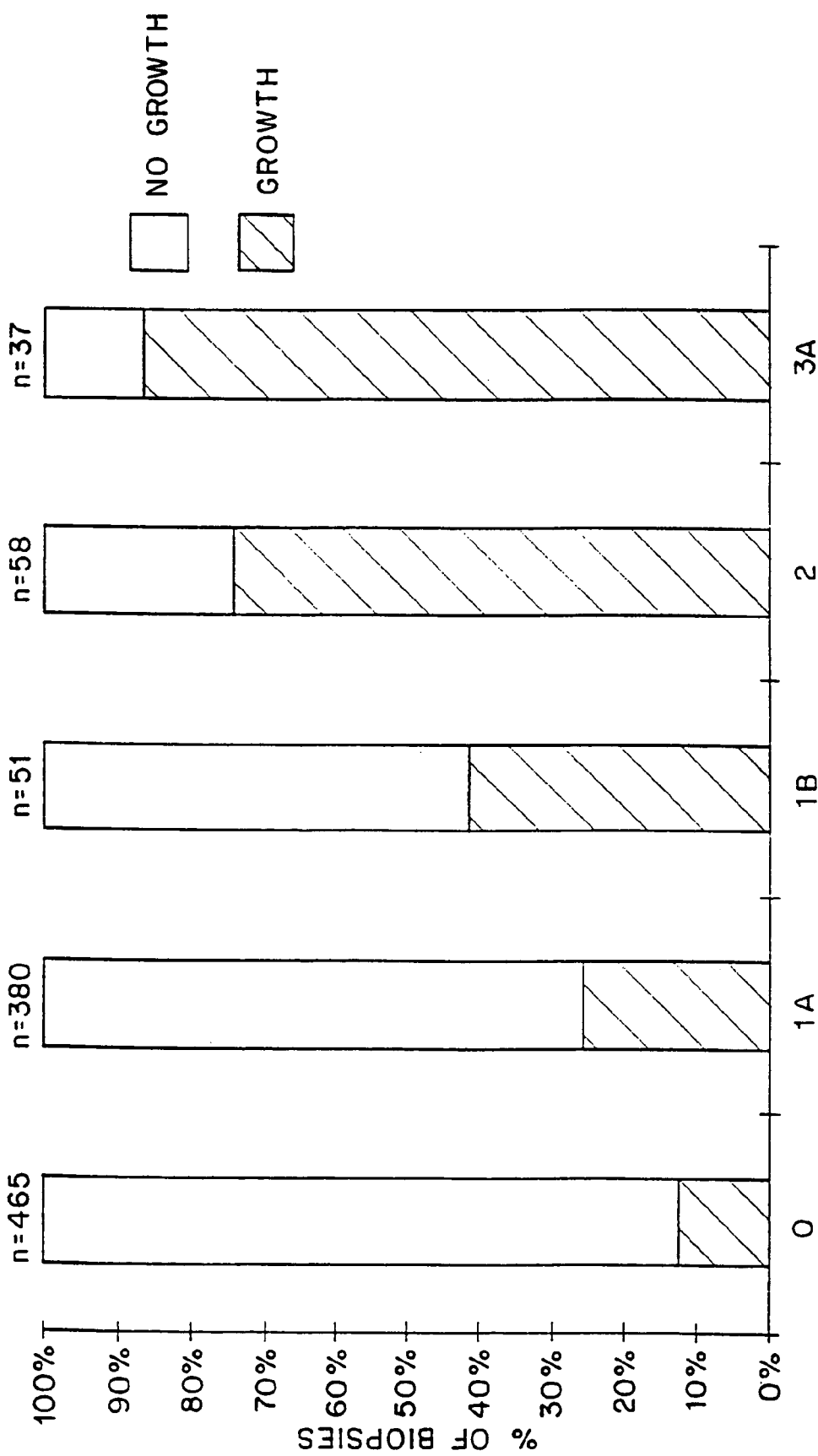

FIG. 3. IL-2 dependent lymphocyte growth from endomyocardial biopsies performed during the first year post-cardiac transplantation, defined as a lymphocyte growth assay (LGA) score of 1 or greater, correlates with biopsy grade (<0.0001).

FIGS. 4A–D. Influence of a positive lymphocyte growth assay (LGA) and of IgG antibodies against non-donor specific MHC class II antigens (IgG anti-II) on progression to a high-grade rejection within 90 days of having a low-grade EMB during the first year post cardiac transplantation.

Figure 4A:
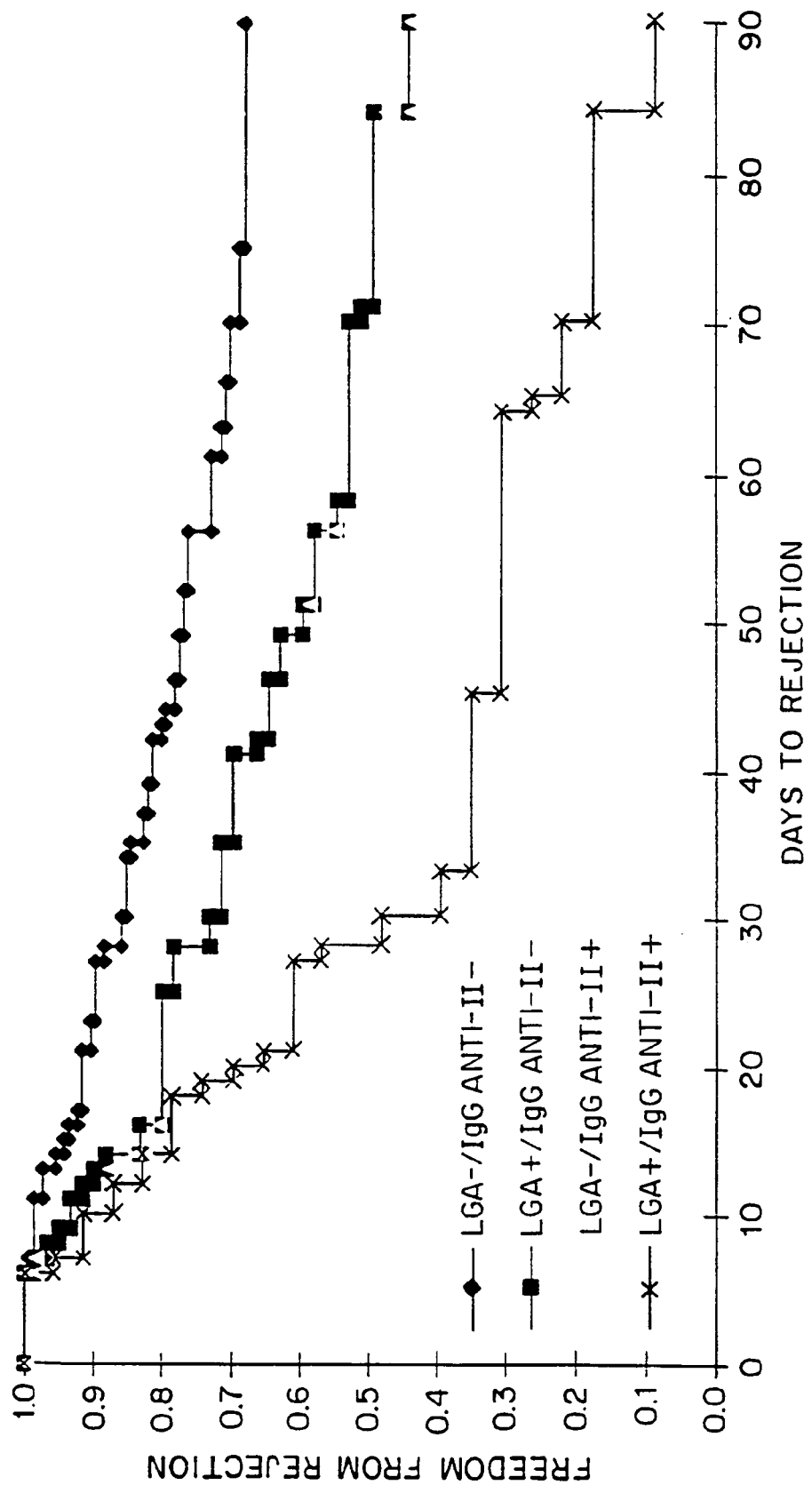

FIG. 4A. Among cardiac transplant recipients with complete donor mismatches at the HLA-DR locus, the concomitant presence of both a positive LGA and IgG anti-MHC class II antibodies significantly increases the risk for subsequent development of a high-grade rejection (p=0.0064).

Figure 4B:
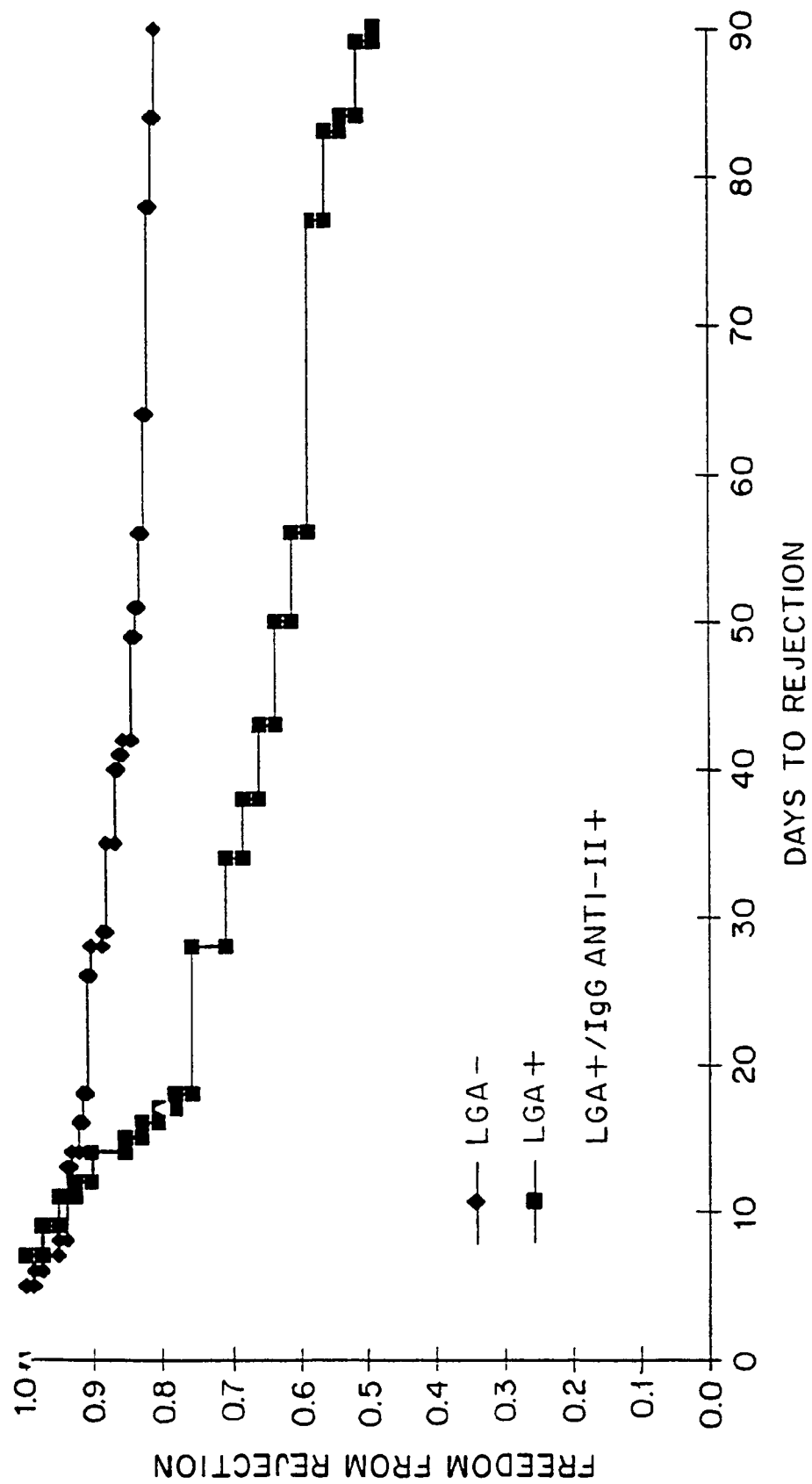

FIG. 4B. Among cardiac transplant recipients with one or more donor matches at the HLA-DR locus, a positive lymphocyte growth assay (LGA) significantly increases the risk for subsequent development of a high-grade rejection (p=0.0003). Concomitant screening for IgG anti-MHC class II antibodies does not increase the risk associated with a positive LGA in this group.

Figure 4C:
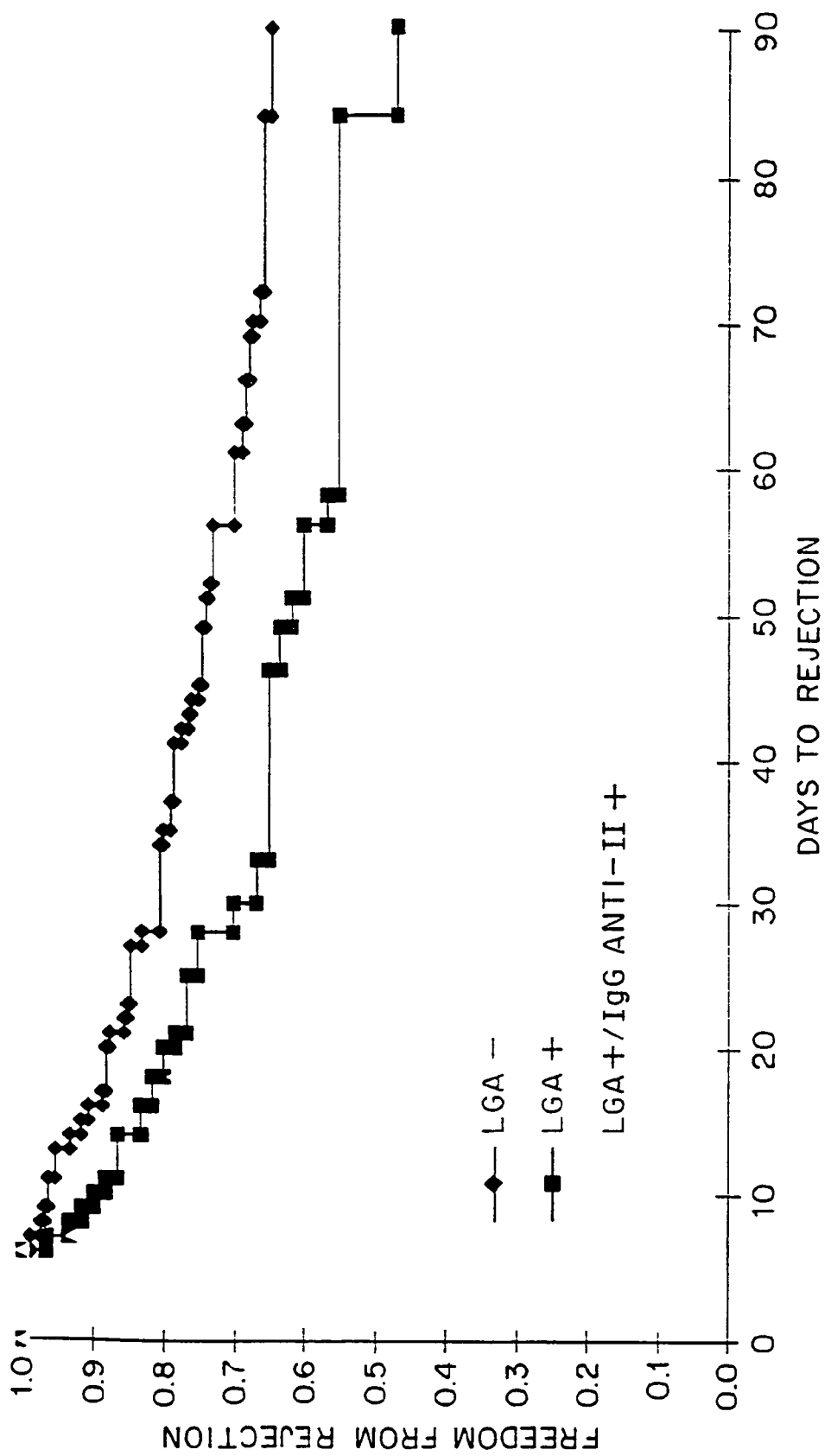

FIG. 4C. Among fully HLA-DR mismatched individuals with a endomyocardial biopsy grade A or 1A, the presence of IgG antibodies against non-donor specific MHC class II antigens (IgG anti-II) accompanying a positive lymphocyte growth assay (LGA) significantly increases the risk for progression to a high-grade rejection within 90 days of having a low-grade EMB during the first year post cardiac transplantation (p=0.0179).

Figure 4D:
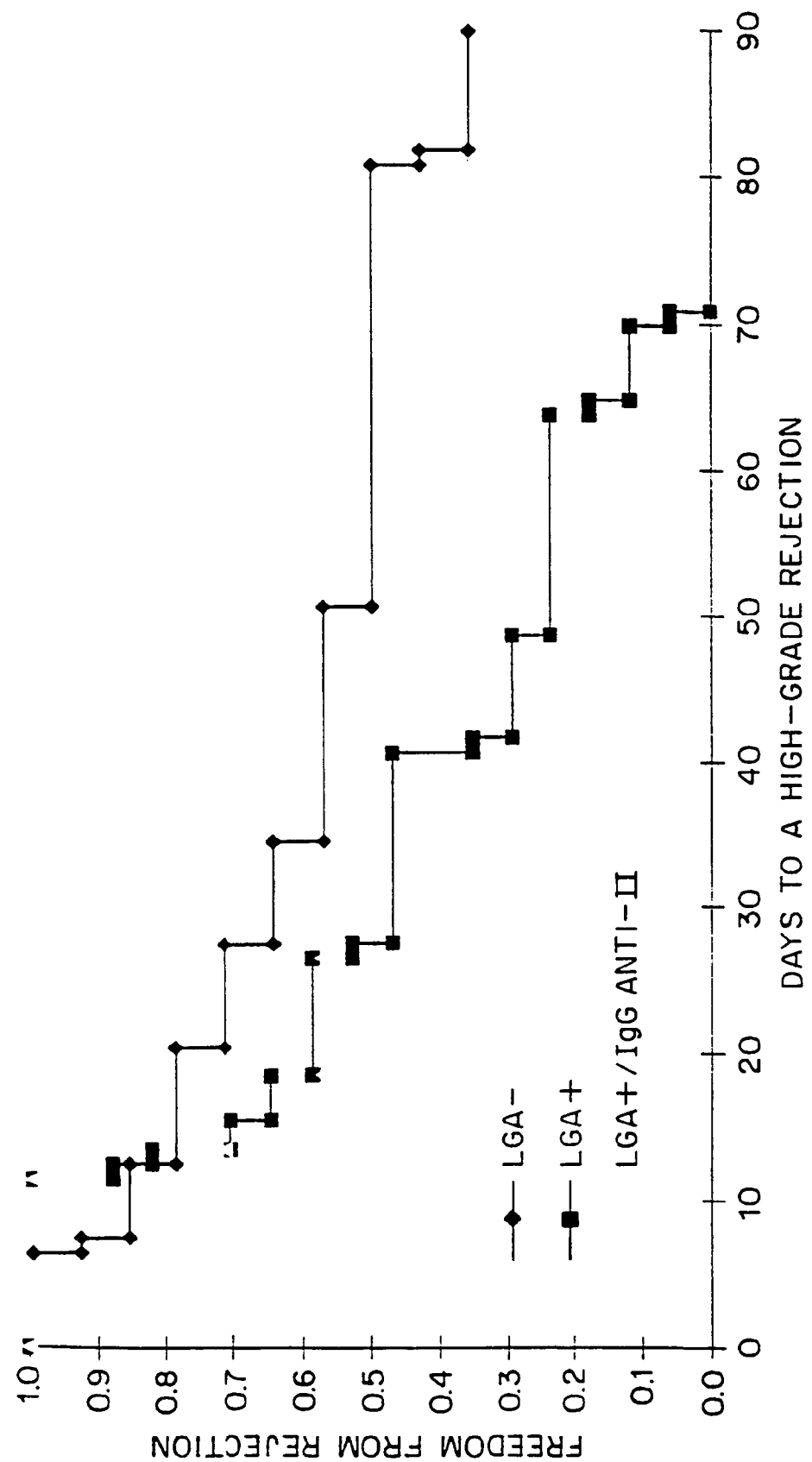

FIG. 4D. Among fully HLA-DR mismatched individuals with an endomyocardial biopsy grade 1B or 2, a positive lymphocyte growth assay (LGA) alone significantly increases the risk for progression to a high-grade rejection within 90 days of having a low-grade EMB during the first year post cardiac transplantation (p=0.0128).

Figure 5:
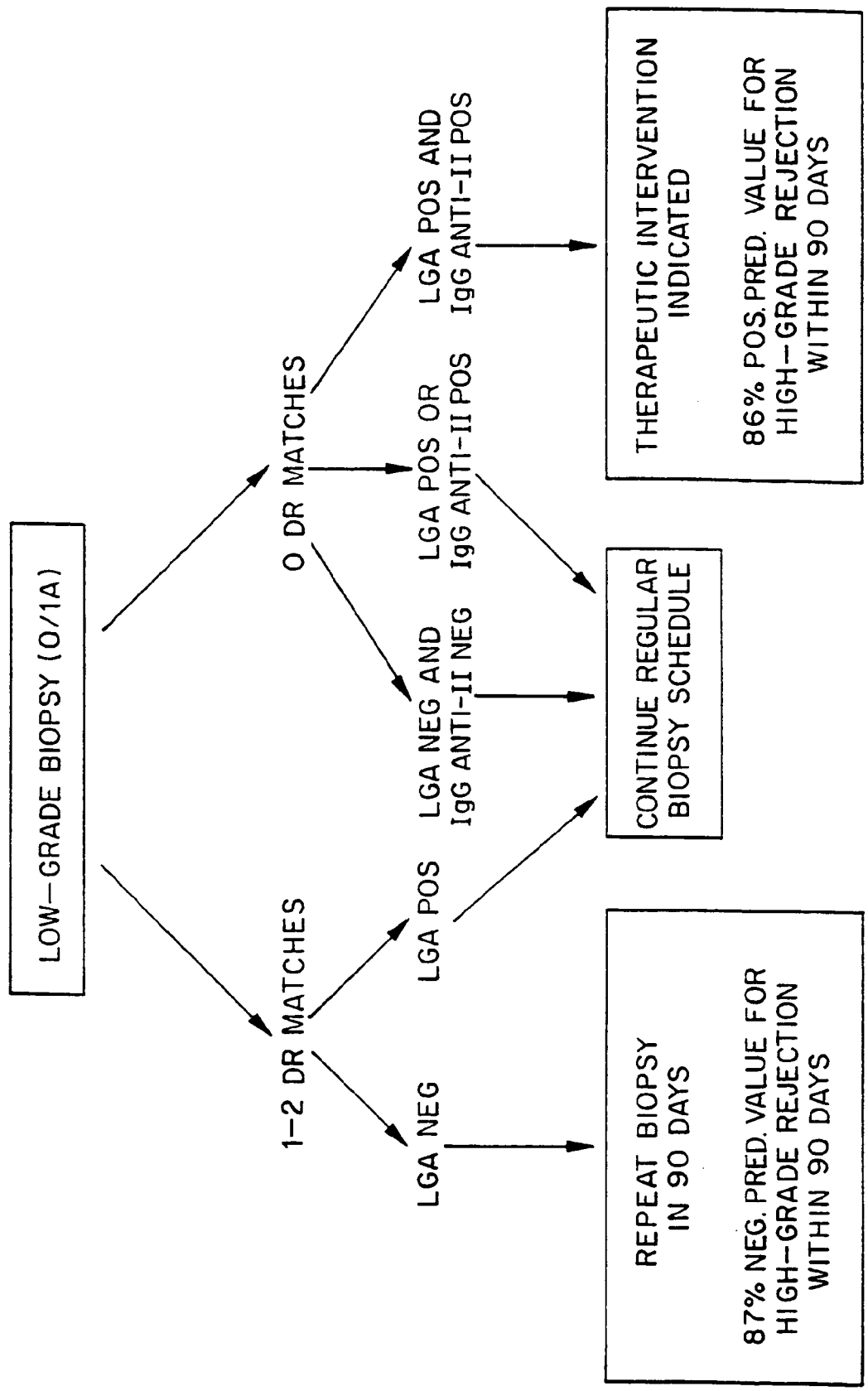

FIG. 5. A clinical algorithm to predict the risk of progression from a low-grade biopsy to a high-grade rejection within 90 days, and suggested treatment modifications strategies.

5. DETAILED DESCRIPTION OF THE INVENTION

The present invention relates to a method for predicting whether or not a transplant recipient is likely to reject a tissue allograft wherein said method is based on results derived from three immunological assays. The three immunological assays include class II HLA-DR typing, a lymphocyte growth assay and IgG anti-MHC class II antibody measurement. The method of the invention may be used to predict the likelihood of rejection in patients receiving a variety of different tissue allografts including, but not limited to, cardiac, liver, lung, kidney or pancreatic transplants. The method of the invention may be used at any time following transplant, but preferably within the first 6–12 months following transplantation.

5.1. Immunological Assays

The present invention relates to the use of three immunological assays for predicting whether or not transplant recipients are likely to reject tissue allografts. The assays include an HLA assay to determine the presence or absence of at least one Class II HLA-DR match between recipient and donor, a lymphocyte growth assay and an assay to detect the presence, in the recipient, of IgG anti-MHC Class II antibodies.

In order to determine the presence or absence of at least one class II HLA-DR match between recipient and donor, the Class II HLA-DR antigens expressed on the recipient's or donor's cell surface can be determined using a variety of different techniques well known to those of skill in the art. Such techniques include, for example, microcytotoxicity assays (Hopkins et al., 1981, Basic Microlymphocytotoxicity Techniques, In A. A. Zachery and W. E. Braun (ed.) AACHT Manual. AACHT, New York); mixed lymphocyte reactions (Bach and Voynow, 1966, Science 153:545–547) and polymerase chain reactions.

Microcytotoxicity assays involve the mixing of pure lymphocytes derived from the recipient or donor with well characterized typing antibodies that are HLA-DR immunoreactive. The mixture is incubated for a sufficient time to allow the antibodies to binds to the lymphocyte surface HLA-DR antigens. This is followed by addition of complement, which may be derived from, for example, rabbit serum. The addition of complement results in complement fixation and any cells with antibody bound to their cell surface will lyse due to the complement fixation reaction. The quantity of lysed cells can be measured using a variety of different methods. For example, a vital dye which is excluded from live cells but stains dead cells can be added to the sample and the number of dead cells versus live cells can be determined.

Additionally, mixed lymphocyte reactions can be used to identify the Class II HLA-DR antigens expressed on the cell surface. Reference cells which express known Class II antigens are used to stimulate lymphocytes derived from the recipient or donor. Such reference cells are publically available from cell depositories such as the American Type Culture Collection. The presence of a proliferative response in the mixed lymphocyte reaction indicates a difference of one or more class II antigens, whereas the absence of a response indicates that the Class II antigens of both parties are the same.

In yet another embodiment of the invention a polymerase chain reaction (PCR) can be used to identify the Class II HLA-DR antigen expressed on the surface of the recipient's or donor's cells. Using sequence specific oligonucleotide primers that will hybridize only to specific DNA sequences shared by Class II HLA-DR alleles, DNA fragments encoding the Class II HLA-DR antigen can be amplified (Bodmer et al., 1994, Tissue Antigens 44:1). The source of the DNA to be used in the PCR reaction is DNA derived from the recipient's or donor's cells using techniques well known to those of skill in the art. The PCR product is then spotted onto a nitrocellulose membrane. The spots are then probed with radiolabelled oligonucleotide probes that are designed to bind specifically to the different Class II HLA-DR alleles. Alternatively, the amplified fragment can be sequenced to determine the identity of the Class II HLA-DR allele.

Once the Class II HLA-DR antigen expressed on the surface of the recipient's cells has been identified, the antigen is compared to those antigens expressed on the surface of donor cells to determine the presence or absence of at least one HLA-DR match between recipient and donor.

The second immunological assay is designed to test for the presence of antigen activated T lymphocytes and is referred to as a lymphocyte growth assay. To perform such assays, a patient derived biopsy sample is placed in medium supplemented with appropriate lymphocyte growth factors, such as for example, recombinant IL-2, IL-15 or donor derived antigens. The sample is then assayed for lymphocyte proliferation. Methods for assaying for lymphocyte proliferation include visualizing the sample at 48 hours with a phase inverted microscope. Growth of antigen activated T lymphocytes is scored on a semiquantitive scale from 0 to 3+ on the basis of circumferential T cell aggregation. A score of 1+ or greater is deemed positive. Other methods well known to those of skill in the art may be used equally as well for detecting lymphocyte proliferation. Such assays include, for example, detection of incorporated radio-labeled nucleotides into the DNA of proliferating lymphocytes.

The third immunological assay to be used in the practice of the invention is designed to detect circulating IgG anti-HLA antibody in the serum of the transplant patient. In such an assay, serum is screened for the presence of anti-HLA antibodies through detection of complement-mediated lytic activity. Serum is screened for complement-mediated lytic activity against T and B lymphocytes from a panel of seventy individuals representing the most frequently encountered HLA class I and HLA class II antigens. The assay is performed in the presence or absence of dithioerythritol.

Persistant serum reactivity following dithioerythritol treatment identifies the presence of IgG alloantibodies, whereas loss of activity indicates the presence of IgM alloantibodies. Anti-HLA class I antibodies were identified when serum reacted with both T and B cell panels. Anti-HLA class II antibodies were identified when serum reacted with B but not T cell panels. Antibodies against both HLA class I and II antigens were identified when serum reacted against both panels and B cell reactivity exceeded T cell reactivity over two-fold.

In one specific, nonlimiting embodiment, IgG anti-MHC Class II (i.e., HLA DR) antibodies may be detected as follows (see also Section 7, infra). Sera may be obtained from a plurality of patients on the day of transplantation and screened for the presence of lymphocytotoxic antibodies against separated T lymphocytes and B lymphocytes obtained from a panel of control individuals representative of the most frequently encountered HLA class I and class II antigens in the general population. Sera may then be screened for complement mediated lytic activity in the presence or absence of dithioerythritol (DTT). Total T cell PRA may be considered positive if serum, in the absence of DTT, reacts against greater than 10% of the T cell reference panel. Anti-MHC antibody specificity for Class I or Class II antigens may be determined as follows. Working definitions for IgG antibodies against HLA class I molecules (IgG anti-I) or class II molecules (IgG anti-II) may be established using, as reference, sera from a plurality of cardiac transplantation patients with PRA values >10% and with anti-MHC class I and class II specificities defined by standard Tail analysis. Since MHC class I antigens are constitutively expressed by both T cells and B cells, IgG antibodies against HLA class I molecules (IgG anti-I) may be considered present in the working definition when DTT-treated serum reacted against greater than 10% of both the T cell reference panel and the B cell panel. To concomitantly identify and discriminate IgG antibodies against HLA class II molecules (IgG anti-II) in the presence of IgG anti-I, an algorithm may be employed which uses the ratio of serum reactivity to B cells versus T cells, since MHC class II antigens are constitutively expressed by B cells, but not T cells. To confirm this working definition using sera with defined IgG anti-MHC class II specificities, a logistic regression analysis may be performed by a maximum likelihood procedure using Biological Management Database Program statistical software to calculate the IgG anti-II predictive value for the ratios of B cell serum reactivity/T cell serum reactivity of 1.25, 1.50, 1.75, 2.00 and 3.00. Maximal sensitivity (91%) for identifying sera with reactivity against MHC class II antigens may be obtained using a ratio of B cell/T cell serum reactivity of 2.00 (model coefficient −3.481, SE 1.19, p=0.0002). Therefore, IgG antibodies against both MHC class I and class II molecules may be considered present if DTT-treated serum reacts against greater than 10% of both the T and B cell reference panels, and the B cell reactivity exceeds the T cell reactivity by at least two-fold. IgG anti-II may also be considered present if DTT-treated serum reacted against greater than 10% of the B cell reference panel, but not the T cell reference panel.

5.2. Analysis of Immunological Data to Determine Risk of Transplantation Rejection The present invention provides a method for use in clinical practice to prospectively identify patients who are at either low, moderate or high risk of progression to a high-grade rejection. The method of the invention relies on data derived from three immunological assays and the use of that data in conjunction with an algorithm to identify patients at high risk for transplantation rejection. Although the comparison of the major histocompatibility antigens HLA-DR, the detection of IgG directed toward MHC Class II antigens, and the lymphocyte growth assay have been known in the art, it had not, prior to the invention, been known that combining these three variables would result in a means to identify low, moderate and high-risk transplant recipients with a predictive value exceeding 80 percent.

As shown in FIG. 5, a negative LGA at the time of a low-grade biopsy in individuals with 1–2 DR matches is associated with an 87% negative predictive value (95% CI 80%–92%) and 16% positive predictive value for progression to a high rejection. Individuals in this category do not require another biopsy for 90 days. When these individuals have a positive LGA continuation of a frequent biopsy schedule is recommended since the risk of progression to a high-grade biopsy is moderately increased. Among fully DR-mismatched individuals, when one or both of the LGA and IgG anti-MHC class II antibodies results are negative the negative predictive value for progression to rejection is 76% and 77%, respectively, and the positive predictive value is 41% and 40%. Since these results indicate a moderate probability of progression to rejection, continuation of a frequent biopsy schedule is recommended, although therapeutic intervention is not suggested. When both the LGA and IgG anti-MHC class II antibody results are positive in this group, the positive predictive value for progression reaches 86% (95% CI 68%–100%). Therapeutic intervention in these individuals is recommended.

A subject who is determined to be at low risk for high grade rejection may be allowed to experience an interval without additional clinical intervention, for a reasonable period of time. A subject determined to be at moderate risk may be subjected to further and/or more frequent diagnostic procedures. A subject determined to be at high risk may be aggressively treated so as to avoid the occurrence of a high-grade rejection episode.

The present invention, by enabling a determination of the risk for high-grade rejection in a transplant patient, reduces unnecessary diagnostic and therapeutic procedures in low risk patients. For example, in a specific, nonlimiting embodiment of the invention involving cardiac transplantation, for individuals whose immunologic profiles indicate a persistently low risk for high grade rejection, the invention has the potential to significantly reduce the number of endomyocardial biopsies being performed during the first year.

In addition, the present invention enables the identification of low risk patients in whom immunosuppressive reagents may be safely withdrawn thereby eliminating the serious side effects associated with the administration of such immunosuppressive reagents. Following withdrawal of the immunosuppressive reagent, the method of the invention may be further utilized by the attending physician to monitor changes in the transplant recipient's risk of rejection. Such screening can be performed, for example, at intervals of every three months. Should the recipient's risk shift from low risk to moderate or high risk the physician may choose to resume treatment with an immunosuppressive agent.

In patients found to be at moderate risk for high grade rejection, the patient will continue on a biopsy schedule. Additional immunological assays can also be conducted to assay for T-cell proliferation. For example, peripheral T cell proliferation in response to donor HLA-DR antigens can be detected. Such assays are designed to improve the sensitivity for detection of T-lymphocyte proliferation. Using such assays, patients may be sub-divided into those patients at low-moderate risk and high-moderate risk of high grade rejection.

Transplant recipients are typically treated with agents such as steroids, cyclosporin and azathioprine. In patients identified at moderate or high risk for high grade rejection, or where an increased risk of graft rejection is observed the doses of agents can be appropriately adjusted to decrease the risk of rejection. Additional agents such as mycophenolic acid can also be administered. Agents such as the steroid solumedrol may also be administered intravenously followed by oral administration of predisone in doses of 60 mg a day, tapering the doses to 10 mg a day.

The prospective identification of patients at high risk for grade 3A rejections will enable rational institution of interventional therapy to reduce anti-donor alloreactivity and prevent high-grade rejection episodes. Since adequate reversal of already established high-grade rejections does not prevent the subsequent sequelae of transplant-related coronary artery disease, only by preventing high-grade rejections from occurring can the incidence of this principal complication be reduced and/or its onset delayed.

Interventional strategies to prevent rejection in high-risk patients, or in some instances moderate risk patients, will need to be directed to at least two phases of cellular interactions: inhibition of T cell activation (direct and indirect reactivity to allogenic HLA-DR molecules), and of B cell functions (anti-DR IgG production, processing and presentation of allogeneic HLA-DR molecules to alloreactive T cells). The latter may be amenable to the use of pharmacologic agents with potent anti-B cell activity such as cyclophosphamide. In contrast, the former may require strategies such as the use of blocking peptides to inhibit T cell activation or induce T cell tolerance to allogeneic HLA-DR molecules. Additionally, monoclonal antibodies against donor or recipient surface structures involved in T-cell activation, or pharmacologic agents such as rapamycin, aimed at reducing T-cell activation may be administered to high risk patients. Agents that reduce IL-2 activity such as anti-IL-2 antibodies can also be used to inhibit T-cell proliferation.

5.3. Antibody Testing Pre- and Post-Transplant

In additional embodiments, the present invention relates to methods of identifying a subject at risk for rejecting a transplant prior to receiving the transplant. These embodiments are based, at least in part, on the recognition that the presence of IgG class antibodies directed toward MHC Class II antigens, prior to transplant, has a positive correlation with high-grade cellular rejection (see, for example, the example in Section 7, infra). The relevant IgG antibodies may be detected by the methods described above or those set forth in Section 7. If a patient is found to have such antibodies prior to transplant, the patient may be treated with an immunosuppressive agent, for example, but not by way of limitation, cyclophosphamide, administered intravenously at a dose of 0.5–1 g/meter, every three to four weeks in advance of the transplant procedure. Such treatment may optionally be continued for three to four months after the transplant procedure.

The detection of IgG anti-MHC Class II antibodies may be used as an index of rejection risk either prior to or after a subject receives a transplant, either considered in conjunction with HLA matching and lymphocyte growth assay results, as set forth above, or independently. Thus, post-transplant, the detection of IgG anti-MHC Class II antibodies in a subject, where a biopsy and/or lymphocyte growth assay have not performed, may itself indicate that immunosuppressive therapy of the subject should be modified, either by changing the immunosuppressive agents or dosages used.

5.4. Kits

The present invention provides for kits for carrying out the above-described assays.

In a first series of nonlimiting embodiments, a kit according to the invention comprises components for detecting and/or measuring IgG antibodies directed toward MHC class II antigen. As one example, where the antibodies are detected and/or measured by enzyme linked immunoabsorbent assay (ELISA), such components may comprise target antigen, in the form of at least one and preferably a plurality of different MHC class II antigens or epitopes thereof, linked to a solid phase, and a means for detecting antibody bound to target antigen and determining that the antibody is an IgG class antibody. Such means for detection may be, for example, an antibody directed toward the constant region of IgG (e.g., rabbit anti-human IgG antibody), which may itself be detectably labeled (e.g., with a radioactive, fluorescent, colorimetric or enzyme label), or which may be detected by a labeled secondary antibody (e.g., goat anti-rabbit antibody).

Alternatively, IgG anti-MHC Class II antibodies may be detected and/or measured using a cell based assay, such as, for example, a microcytotoxicity assay or a flow cytometry assay. Where the assay is a microcytotoxicity assay, the kit may comprise cells bearing at least one and preferably a plurality of different MHC Class II antigens, and complement, such that when serum from a subject is added to the cells, the binding of antibodies in the serum to the cells may result in complement fixation and cell lysis. Lysis may be detected by an attrition in cell number, by the release of a metabolic marker (for example, if $^{51}$"Cr is incorporated into the antigen-bearing cells), or similar means (the kit may therefore comprise a vital dye or $^{51}$Cr). The distinction between IgG and IgM antibodies may be made by performing the assay in the presence of a denaturing agent, such as dithiothreitol, which denatures IgM but not IgG. Where the assay is a flow cytometry assay, the kit may comprise cells bearing at least one and preferably a plurality of different MHC class II antigens, and a means for detecting antibodies from a subject's serum which are bound to the cells under assay conditions. As one nonlimiting example, the kit may comprise a fluorescently labeled anti-IgG antibody, which may be a polyclonal or monoclonal antibody (e.g., rabbit anti-human IgG antibody), such that when the cells provided are combined with serum of the subject under conditions which allow antibody binding, and also combined with the fluorescently labeled antibody, cells bound to subject IgG antibody may be rendered fluorescent and detectable by standard flow cytometry methods. In related embodiments the cells may be omitted from such kits and donor cells may be used.

In a second series of nonlimiting embodiments, a kit according to the invention may comprise components which detect and/or measure lymphocyte proliferation, as in a lypmhocyte growth assay. Such components may comprise agents which induce lymphocyte proliferation, including, but not limited to, growth factors (e.g., interleukin-2 or interleukin-15) or antigen (e.g., a plurality of MHC antigens) and agents for detecting lymphocyte proliferation, including, but not limited to, labeled nucleotide or other metabolite, or a vital dye. In related embodiments the antigen may be omitted from such kits and donor antigen may be used.

In a third series of nonlimiting embodiments, a kit according to the invention may comprise components which detect and/or measure IgG antibodies directed toward MHC class II antigen and components which detect and/or measure lymphocyte proliferation. Such kits may optionally further comprise components for detecting HLA mismatches.

6. EXAMPLE

Prediction of Progression from a Low-Grade Endomyocardial Biopsy to High-Grade Rejection in Cardiac Transplant Recipients 6.1 Materials and Methods 6.1.1. Patient Population The relationship between cumulative annual high-grade rejection frequency and transplant-related coronary artery disease (TCAD) was investigated in 198 adult cardiac allograft recipients (162 male, 36 female) transplanted at Columbia-Presbyterian Medical Center, New York, between 1992–1996. The predictive value of specific immunologic assays on the subsequent development of high-grade cellular rejection during the first post-transplant year was investigated in 102 patients (82 males and 20 females). All recipients received standard triple immunosuppressive therapy (cyclosporine, steroids, and azathioprine). Cellular rejection episodes of biopsy grade 3A or greater were treated with either steroid pulses (oral or intravenous) or cytolytic therapy (OKT3 or anti-thymocyte globulin). Treatment of cellular rejection episodes of biopsy grades below 3A depend on individual physicians, patient symptomatology, and abnormal hemodynamic values.

6.1.2 Endomyocardial Biopsies

During the first post-transplant year, endomyocardial biopsies (EMB) were performed weekly for the first month, every ten days for the second month, every three weeks for the subsequent two months, then at progressively longer intervals until a baseline schedule of every 2–3 months was reached. Four biopsy fragments were processed for histologic analysis and histologic grades were assigned by the Billingham criteria (Billingham M. E., 1990, J. Heart Transplantation 9:272–276). High-grade cellular allograft rejection was defined pathologically as grade 3A or higher.

6.1.3. Diagnosis of Transplant-Related Coronary Artery Disease (TCAD)

Coronary angiography in two planes was conducted at yearly intervals following transplantation for all patients without clinical features of coronary artery disease, or at unscheduled intervals if clinically indicated. Transplant-related coronary artery disease (TCAD) was diffused as either diffused concentric narrowing of tertiary branches or significant obstruction of three or more major epicardial vessels.

6.1.4. Immunological Assays 6.1.4.1 HLA Typing

Serological typing of HLA-A and HLA-B loci was performed by standard microcytotoxicity techniques. HLA-DR typing was performed by both serologic analysis and DNA techniques using sequence-specific oligonucleotide primers and the polymerase chain reaction.

6.1.4.2. Lymphocyte Growth Assay (LGA)

One biopsy fragment was placed in medium supplemented with recombinant IL-2 (5 units/ml) and examined visually at 48 hours with a phase-inverted microscope. Growth was scored on a semiquantitive scale from 0 to 3+ on the basis of circumferential T cell aggregation (Fischer, P. E., 1995, J. Heart and Lung Transplantation 14:1156–1161). A score of 1+ or greater was considered positive.

6.1.4.3. Anti-HLA Antibody Measurement

At the time of each EMB, serum was screened for complement-mediated lytic activity, in the presence or absence of dithioerythritol, against T and B lymphocytes from a panel of 70 individuals representative of the most frequently encountered HLA class I and class II antigens. Persistent serum reactivity following dithioerythritol treatment identified IgG alloantibodies, whereas loss of reactivity identified IgM alloantibodies. Working definitions for IgG and IgM antibodies against HLA class I molecules or class II molecules were established in our laboratory using, as reference, sera from 28 cardiac transplant recipients with panel reactivity values >10% and with anti-HLA class I and class II specificities. Anti-HLA class II antibodies against both HLA class I and II antigens were identified when serum reacted against both panels, and B cell reactivity exceeded T cell reactivity by over two-fold. Overall, using these combined criterial for identifying anti-HLA class II antibodies (i.e. reactivity only with B cells or at least two-fold higher reactivity with B cells than T cells) correctly identified patients with HLA class II serum reactivity with 94% sensitivity and 88% specificity. The presence of autoantibodies was excluded by autologous serum cross-match with recipient T and B cells.

6.1.5 Study Design

The study objectives were to: (1) retrospectively investigate the relationship between cumulative annual high-grade rejection frequency and transplant-related coronary artery disease (TCAD), and (2) prospectively study whether concomitant use of donor-recipient HLA-DR matching data, lymphocyte growth assays (LGA), and anti-HLA antibodies, can predict progression to a high-grade rejection within 90 days of a low-grade EMB during the first year post-cardiac transplantation. This interval exceeds the longest duration between consecutive biopsies during the first post-transplant year.

For the first part of the study, patients whose initial angiogram was performed prior to the first scheduled post-transplant annual examination were excluded so that all patients in this analysis were followed for at least one year post transplant. The onset for TCAD was calculated as the midpoint between the date of the first positive angiogram and the previous negative study. Cumulative annual high grade rejection frequency for each individual was calculated as the number of high grade rejections prior to the onset of TCAD divided by the duration from transplantation to the development of TCAD or, for those remaining free from TCAD, to the end of the study period.

For the second part of the study, results of EMBs, LGAs, and anti-HLA antibody measurements were compiled prospectively from January 1996 to January 1997 for all patients who were within their first post-transplant year (n=102). When a followup EMB was not performed within 90 days, LGAs and anti-HLA antibody measurements accompanying a particular EMB were excluded from the study. Similarly, when an EMB result was treated (either because of histopathologic grade 3A or higher, or because of abnormal hemodynamics or patient symptoms), accompanying LGAs and anti-HLA antibody measurements, as well as those performed in the ensuing 90 days, were executed. A total of 896 low-grade EMBs (<grade 2) were analyzed prospectively for subsequent progression to grade 3A rejection within 90 days.

6.1.6 Statistical Analyses

Kaplan-Meier univariate statistics were used to evaluate the relationship between cumulative high-grade rejection frequency and onset of TCAD, with p values calculated by log rank statistics (Kaplan, et al., 1958, J. American Statistics Association 53:457–481). Multivariable analysis of risk factors for a high-grade rejection over the 90 days following a low-grade EMB was performed using the Generalized Estimation Equations approach (Liang, et al., 1986, Biometrika 73:13–22) which incorporates a logistic regression model for the binary outcome, correcting for the correlation among observations in the same individual. For this analysis, events (high-grade rejections) were defined as the biopsy result nearest to 90 days following a low-grade biopsy. Variables considered as potential associated risk factors for a subsequent high grade rejection at the time of the low-grade biopsy included ischemic time, donor/recipient age, sex, race, matching at HLA-A, B, or DR loci, anti-HLA antibodies, and LGA. For variables determined to be associated with high-grade rejection in this analysis, positive and negative predictive values were evaluated using 2×2 contingency tables, as well as by Kaplan-Meier actuarial life tables. All data were analyzed using SAS system software (SAS Institute Inc, Cary, N.C.).

6.2. Results 6.2.1 Cumulative High Grade Cellular Rejections are a Risk Factor from Early Development of TCDA An investigation was conducted to determine whether cumulative, established, high-grade rejections occurring in cardiac allograft recipients are a risk factor for the subsequent development of TCAD, irrespective of their successful treatment and resolution. Patients were stratified into four groups according to increasing cumulative annual high-grade rejection frequencies (i.e., <0.25/yr, 0.25–0.5/yr, 0.5–0.75/yr, >0.75/yr). By Kaplan-Meier time-dependent analysis, a threshold of >0.75 high-grade rejections per year was associated with significantly shorter time to TCAD (p=0.0002), FIG. 1. The median duration to TCAD was 1.5 years for those with >0.75 rejections/year vs 3.3 years for those with <0.75 rejections/year. By 3 years post-transplantation, 94% of individuals with >0.75 rejections/year had developed TCAD compared with only 45% of those with <0.75 rejections/year, Table 1. No significant differences in TCAD onset were found among the three groups with cumulative annual rejection frequencies <0.75/year, each group having median durations to TCAD of >3 years and rates of TCAD development by 3 years of 25%–45%. These results demonstrated an association between a high cumulative annual rejection frequency (>0.75/year) and TCAD, and provided the impetus top an algorithm for prospective identification of patients at high risk for progression from a low-grade EMB to a high-grade rejection.

6.2.2. Donor/Recipient Matching at the HLA-DR Locus Protects Against Progression to High-Grade Rejection Since a high-grade rejection is far more likely to occur within the first year post-cardiac transplantation 12–15, a study was conducted to determine whether matching at the HLA-DR, HLA-B or HLA-A loci protected against progression of a low-grade EMB to a high-grade rejection during this period. Among individuals with one or more HLA-DR matches, 27% of low-grade EMBs progressed to a high-grade rejection within 90 days compared with 47% of low-grade EMBs in those fully DR. mismatched (odds ratio 2.42, p<0.0001), FIG. 2. In contrast, donor/recipient matching at an MHC class I locus (HLA-A or HLA-B) did not influence progression to high-grade rejection (39% with no matches vs 36% for those with one or more matches, odds ratio 1. 16, p=0.35). The results validated our overall approach of identifying risk factors for progression of EMB to high-grade rejection, and enabled stratification of fully DR-mismatched recipients into a category requiring further immunologic monitoring.

6.2.3 IL-2 Dependent Lymphocyte Growth Assay Correlates with Histologic Rejection of Endomycardial Biopsy To use the LGA in a predictive fashion, it was necessary to determine how closely this assay correlated with concomitant histopathologic EMB grade. IL-2 dependent lymphocyte, defined as an LGA score of I or greater, strongly correlated with EMB grade (p<0.0001), FIG. 3. The positive yield increased progressively with increase in pathologic biopsy grade, from grade 0 to 86% for grade 3A. Since 13%–42% of positive LGA scores accompanied low EMBs (grades 0, IA or 113), the predictive value of these results on subsequent progression to a high-grade rejection was studied.

6.2.4. A Positive Lymphocyte Growth Assay Accompanying a Low-Grade Biopsy is Associated with Progression to a High-Grade Rejection within 90 Days As shown in Table 2, a positive LGA accompanying a low-grade biopsy (grades 0, 1A, or 1B) was associated with a significantly increased risk of developing a high-grade rejection (3A or >) within 90 days. Among individuals with one or more HLA-DR matches, 58% of EMBs accompanied by a positive LGA progressed to a high-grade rejection compared with 21% of those with negative LGA (p<0.0001, odds ratio 5.22). Among individuals with complete HLA-DR mismatches, 64% of EMBs accompanied by a positive LGA progressed to a high-grade rejection compared with 40% of those with a negative LGA (p=0.0002, odds ratio 2.73). While these confirm the utility of a positive LGA to identify individuals at risk of a high-grade rejection, they also indicate that by itself this assay lacks sufficient discriminatory value to guide therapeutic interventional strategies.

6.2.5 IgG Anti-MHC Class II Antibodies Accompanying A Low-Grade Biopsy are Associated with Progression to High-Grade Cellular Rejection within 90 Days The relationship between anti-HLA antibodies measured at the time of a low-grade biopsy and subsequent high-grade rejection was investigated. As shown in Table 3, the presence of circulating IgG antibodies against MHC class II molecules (IgG anti-II) were associated with progression to a high-grade rejection within 90 days in individuals with complete donor-recipient HLA-DR mismatches, but not in those with at least one HLA-DR match. Among fully DR-mismatched individuals, 66% of low-grade EMBs accompanied by IgG anti-MHC class II antibodies progressed to a high-grade rejection compared with 42% of those without these antibodies (p<0.01, odds ratio 2.68). Although in the initial analysis IgG anti-class I antibodies were associated with progression to high-grade rejection (odds ratio 1.92), this association in fact reflected the concomitant presence of IgG anti-MHC class II antibodies and was no longer evident after exclusion of individuals with IgG anti-MHC class II antibodies (progression to high-grade rejection occurred in 31% of EMBs with IgG anti-MHC class I antibodies vs 34% without IgG anti-MHC class I antibodies, p=0.42, odds ratio 0.83). IgM anti-HLA antibodies were noted with subsequent high-grade cellular rejections.

6.2.6 A Positive Lymphocyte Growth Assay and IgG Anti-MHC Class II Antibodies are Additive Risk Factors for High-Grade Rejection within 90 Days in Fully DR Mismatched Recipients with Biopsy Grades 0 or IA Patients were stratified by the presence or absence of complete donor/recipient DR, mismatch and an investigation was carried out to determine whether the presence of both a positive LGA and IgG anti-MHC class II antibodies at the time of a low-grade biopsy were additive risk factors for progression to a high-grade rejection. Among fully DR mismatched patients, when both the LGA and IgG anti-MHC class II antibodies were negative 25% of low-grade EMBs progressed to a high-grade rejection within 90 days, FIG. 4A. When either the LGA or IgG anti-MHC class 11 antibodies were positive, 55% progressed to a high-grade rejection, median durations 71 and 81 days respectively. When both LGA and IgG anti-MHC class 11 antibodies were positive, 90% of EMBs progressed to a high-grade rejection, median duration 28 days (p=0.0064). Among recipients with one or more donor DR matches, a positive LGA was associated with progression to high-grade rejection (p=0.0003), however this association could not be increased beyond 50% by the concomitant screening for IgG anti-MHC class II antibodies, FIG. 4B.

Next, it was determined whether the additive effect of these three concomitant assays was similar for each initial biopsy grade. As shown in FIG. 4C, in fully DR-mismatched individuals with an EMB grade 0 or 1A, IgG anti-MHC class 11 antibodies accompanying a positive LGA increased the odds ratio of a high-grade rejection by 5.3 fold compared to a positive LGA alone. The median duration to a high-grade rejection was 84 days following a positive LGA alone and 30 days following the additional presence of IgG anti-MHC class II antibodies (p=0.0 179). Among fully DR-mismatched individuals with EMB grades 1B or 2, a positive LGA alone was followed within 90 days by a high-grade cellular rejection in 100% of cases, FIG. 4D. The median duration to a high-grade rejection was 28 days in cases when the LGA was positive, regardless of the presence of IgG anti-MHC class II antibodies, compared with 81 days in cases when the LGA was negative (p=0.0 128).

6.2.7 Multivariable Analysis of Risk Factors for High-Grade Cellular Rejection

By multivariable analysis using the Generalized Estimation Equations approach[33], a positive LGA (odds ratio 4.3), the presence of IgG anti-MHC class II antibodies (odds ratio 2.2), and a complete mismatch between donor and recipient at the HLA-DR locus (odds ratio 1.9) were each identified to be independent risk factors for progression to high-grade rejection within 90 days of a low-grade EMB, Table 4. Neither donor-recipient matching at MHC class I loci nor other anti-HLA antibody types were risk factors. None of the non-immunologic variables tested in this multivariable analysis entered the model in the presence of the three identified immunologic risk factors.

6.2.8. A Clinical Algorithm to Predict the Risk of Progression from a Low-Grade Biopsy to a High-Grade Rejection within 90 Days On the basis of the previous data, we sought to establish an algorithm which could be used in clinical practice to prospectively identify patients who are at either low or high risk of progression to a high-grade rejection within 90 days. As shown in FIG. 5, a negative LGA at the time of a low-grade biopsy in individuals with 1–2 DR matches is associated with an 87% negative predictive value (95% CI 80%–92%) and 16% positive predictive value for progression to a high rejection. Individuals in this category do not require another biopsy for 90 days. When these individuals have a positive LGA we recommend continuation of a frequent biopsy schedule since the risk of progression to a high-grade biopsy is moderately increased. Among fully DR-mismatched individuals, when one or both of the LGA and IgG anti-MHC class II antibodies results are negative the negative predictive value for progression to rejection is 76% and 77%, respectively, and the positive predictive value is 41% and 40%. Since these results indicate a moderate probability of progression to rejection we recommend continuation of a frequent biopsy schedule and do not suggest therapeutic intervention. When both the LGA and IgG anti-MHC class II antibody results are positive in this group, the positive predictive value for progression ton reaches 86% (95% CI 68%–100%). We recommend therapeutic intervention in these individuals.

7. EXAMPLE

Relevance of Pre-Transplant IgG Anti-MHC Antibodies 7.1. Materials and Methods
7.1.1. Patient Population 68 patients at high risk of having elevated levels of anti-HLA antibodies were studied. These consisted of two distinct patient populations awaiting cardiac transplantation: 45 primary allograft recipients supported by left ventricular assist devices (LVAD) prior to transplantation and 23 recipients of a second cardiac allograft. All LVAD recipients had a TCI device implanted between 1990 and 1996. The interval of LVAD support ranged from 5 to 541 days with an average of 131.4 days+/–112.3. Among the retransplant population, all patients received their primary allografts between 1983 and 1995, and second grafts between 1989 and 1996. The time between the first and second transplants ranged from 9 months to 10.5 years and averaged 5.07+/–2.50 years. The age distribution was similar among the LVAD (52.62+/–10.66) and retransplant (48.91+/–9.81) patients. For the total group of 68 patients, age ranged from 17 to 67 years with a mean of 51.37+/–10.46. Both groups had a marked male/female preponderance: LVAD 37/8, retransplants 18/5.

Standard triple therapy immunosuppression (cyclosporine, steroids, and either azathioprine or mycophenolate mofetil) was initiated perioperatively for all patients in both the LVAD and retransplant groups. Cellular rejection episodes were treated either with steroid pulses (oral or intravenous) or cytolytic therapy (OKT3 or ATGAM).

7.1.2. Diagnosis of Cellular and Humoral Rejection

Endomyocardial biopsies (EMB) were performed by the Stanford Caves technique weekly for the first month after transplantation, every ten days for the second month, every three weeks for the subsequent two months, then at progressively longer intervals until a baseline schedule of every six months was reached. Four biopsy fragments were processed for histologic analysis and histologic grades of cellular rejection were assigned by the Billingham criteria.

Humoral rejection was diagnosed by immunofluorescence examination of biopsy specimens demonstrating deposition of complement and immunoglobulin in the absence of mononuclear cell infiltration. Immunofluorescent studies were performed when clinical parameters were suggestive of humoral rejection.

7.1.3. HLA Typing

Serological typing of HLA-A and HLA-B loci was performed by standard microcytotoxicity techniques. HLA-DR typing was performed by both serologic analysis and DNA techniques using sequence-specific oligonucleotide primers and the polymerase chain reaction. Donor-recipient HLA matching was evaluated by comparison of serological typing.

7.1.4. Detection of Anti-HLA Antibodies

Sera were obtained from all patients on the day of transplantation and screened for the presence of lymphocytotoxic antibodies against separated T lymphocytes and B lymphocytes obtained from a panel of 70 control individuals representative of the most frequently encountered HLA class I and class II antigens in the general population. Sera were screened for complement mediated lytic activity in the presence or absence of dithioerythritol (DTT). Total T cell PRA was considered positive if serum, in the absence of DTT, reacted against greater than 10% of the T cell reference panel.

7.1.5. Determination of Anti-HLA Antibody Specificity for MHC Class I or Class II Antigens Working definitions for IgG antibodies against HLA class I molecules (IgG anti-I) or class II molecules (IgG anti-II) were established in our laboratory using, as reference, sera from 28 cardiac transplantation patients with PRA values >10% and with anti-MHC class I and class II specificities defined by standard Tail analysis. Since MHC class I antigens are constitutively expressed by both T cells and B cells, IgG antibodies against HLA class I molecules (IgG anti-I) were considered present in our working definition when DTT-treated serum reacted against greater than 10% of both the T cell reference panel and the B cell panel. This working definition for IgG anti-I correlated in 100% of cases (20/20) with patient sera having defined specificity for MHC class I antigens.

To concomitantly identify and discriminate IgG antibodies against HLA class II molecules (IgG anti-II) in the presence of IgG anti-I, we established an algorithm which used the ratio of serum reactivity to B cells versus T cells, since MHC class II antigens are constitutively expressed by B cells, but not T cells. To confirm this working definition using sera with defined IgG anti-MHC class II specificities, a logistic regression analysis was performed by a maximum likelihood procedure using Biological Management Database Program statistical software to calculate the IgG anti-II predictive value for the ratios of B cell serum reactivity/T cell serum reactivity of 1.25, 1.50, 1.75, 2.00 and 3.00. Maximal sensitivity (91%) for identifying sera with reactivity against MHC class II antigens was obtained using a ratio of B cell/T cell serum reactivity of 2.00 (model coefficient −3.481, SE 1.19, p=0.0002). Therefore, IgG antibodies against both MHC class I and class II molecules were considered present if DTT-treated serum reacted against greater than 10% of both the T and B cell reference panels, and the B cell reactivity exceeded the T cell reactivity by at least two-fold. IgG anti-II were also considered present if DTT-treated serum reacted against greater than 10% of the B cell reference panel, but not the T cell reference panel. Testing the validity of this approach using sera analyzed by Tail analysis confirmed that 100% of samples reactive only with B cells (n=11) actually had anti-MHC class II specificity. Overall, using these combined criteria for identifying IgG anti-II (i.e. reactivity only with B cells or at least two-fold higher reactivity with B cells than T cells) correctly identified patients with MHC class II serum reactivity with 94% sensitivity and 88% specificity.

7.1.6. Study Design and Statistical Analysis

The frequency of serum reactivity for IgG anti-I, IgG anti-II, or total T cell PRA was compared between NYHA class IV controls awaiting cardiac transplantation (n=66) and either LVAD recipients (n=45) or retransplant candidates (n=23). For each variable tested, a two by two table was constructed to compare the frequencies in the experimental group with the frequencies in heart failure controls. Odds ratios were calculated by dividing the product of A×D by the product of B×C, where A and B are individuals in each group positive for the variable tested, and C and D are individuals in the groups negative for the variable. Chi squared analysis was used to determine the p value. Group differences for continuous variables, e.g. waiting time to transplantation, were analysed by StudentŌs t test.

The influence of various potential immunologic risk factors on the time to the first high-grade (3A/3B) cellular rejection post-transplant was determined by Kaplan-Meier actuarial analysis, with p values calculated by log rank statistics[11]. The Cox Proportional Hazard model was utilized for the multivariable analysis of time to first high-grade rejectioN (Cox, 1972, J. Royal Statistical Soc. 34:187–220). Any possible grouping effects (i.e. LVAD vs. Retransplant patients) were corrected by stratification in the Cox model. The risk factors analyzed included the presence or absence of each antibody type pretransplant (total T cell PRA, IgG anti-I, IgG anti-II, IgM anti-I, IgM anti-II), donor and recipient age, sex, and race, donor-recipient matching at the HLA-A, B, and DR loci, and ischemic time.

Since nonfatal morbid events such as cellular rejections can occur repeatedly in the same patient, cumulative high-grade (3A/3B) rejections were modeled by the Method of Wei, Lin, and Weissfeld (Wei et al., 1989, J. Am. Statistical Assoc. 84:1065–1073) which models these cumulative high grade rejections by taking into account the fact that repeated episodes may be correlated within each patient. It computes robust variance estimates that allow for the dependence among multiple event times. For all statistical analyses, data was analyzed using SAS System software (SAS Institute, Inc., Cary, N.C.)

7.2. Results

Anti-HLA Antibodies in Sensitized Individuals: The Frequency of Anti-MHC Class I IgG Antibodies Are Increased Only Among LVAD Recipients, Whereas the Frequency of Anti-MHC Class II IgG Antibodies Is Increased in Both LVAD Recipients and Retransplant Candidates. As shown in Table 5, in comparison to NYHA class IV controls awaiting cardiac transplantation, the frequencies of IgG anti-I and total T cell PRA were significantly higher in recipients of LVADs, but not in retransplant candidates. In contrast, the frequency of IgG anti-II was significantly higher in both LVAD recipients and retransplant candidates than in NYHA class IV heart failure 110 controls (respectively, 33% and 29% versus 3%, p<0.0001).

We next sought to determine whether the production of either IgG anti-I or anti-11 was influenced by perioperative transfusion of blood products. Among the LVAD recipients who developed anti-HLA antibodies as defined by a positive T cell PRA, 90% had received peri-operative blood products, with a mean of 16 units of red blood cell transfusions (range 0–88) and 12 units of platelets (range 0–36). By Kaplan-Meier univariate analysis, at the median duration of LVAD implantation of 4 months, 8% of patients who received less than 6 platelet units developed IgG anti-I antibodies compared to 63% who received greater than 6 units (p=0.002). This association was confirmed using the Cox proportional hazards model for multivariable analyses (p=0.04). In contrast, perioperative red blood cell transfusions did not influence the production of IgG anti-I in these analyses. The development of IgG anti-II was not influenced by either the number of peri-operative red blood cell or platelet transfusions.

The Presence of IgG Anti-MHC Class I Antibodies Increases Waiting Time to Cardiac Transplantation. At our institution a positive prospective donor-specific cross-match is considered a contraindication to cardiac transplantation. Therefore, individuals whose sera repeatedly cause positive cross-match reactions have longer waiting times to obtaining a cross-match negative donor organ. Since prospective cross-matches are only performed using unseparated donor lymphocytes, which are predominantly T cells expressing MHC class I antigens, we investigated the effects of IgG anti-I on waiting time to cardiac transplantation. As expected, LVAD patients with IgG anti-I had a significantly longer waiting time than those without these antibodies (175 versus 90 days, p=0.009). Similarly, LVAD patients with a total T-cell PRA also had a longer waiting time than those without these antibodies (190 versus 87 days, p=0.015). In contrast, the presence of IgG anti-II did not affect the waiting time to transplantation (LVAD 139 versus 114 days, p=0.50).

The Presence of IgG Anti-MHC Class II Antibodies at the Time of Transplantation Predicts Shorter Duration to a First High-Grade Cellular Rejection for LVAD and Retransplant Patients. Durations to a first high-grade cellular rejection were similar for both LVAD recipients and retransplant patients, with one quarter of both populations rejecting by 80 days. For this reason, the influence of each antibody type on this outcome was examined not just in each group separately, but on the combined group of all high risk patients.

IgG anti-II detected at the time of transplantation was highly predictive of early high-grade cellular rejection in the post-transplant period for the combined group of patients receiving a second graft or previously on LVAD support. This observation held when each group was studied separately. The median time for a high-grade rejection was 70 days for patients positive for IgG anti-II. In contrast, the actuarial freedom from rejection never fell below 50% in over 1700 days of followup for patients without IgG anti-II (odds ratio >24.3, p=0.006). The presence of IgG anti-I was also a moderate risk factor for a high-grade rejection, however this was not statistically significant (p=0.08). Finally, the presence of a positive total T cell PRA at the time of transplant was not at all predictive of early high-grade rejection. Additionally, neither the presence of IgM anti-I nor IgM anti-II at the time of transplant influenced the time to a high-grade cellular rejection (p=0.94 and p=0.79, respectively).

The Presence of IgG anti-MHC Class II Antibodies is a Major Risk Factor for Post-Transplant Cellular Rejections by Cox Proportional Hazard Modelling for Multivariable Analysis. By Cox Proportional Hazard modelling for multivariable analysis, the only risk factors identified to predict an early high-grade cellular rejection were the presence of pretransplant IgG anti-II (p=0.018) and, to a lesser extent, IgG anti-I (p=0.086), see Table 6. These observations held for both LVAD and retransplant recipients. None of the other variables tested in this analysis were predictive of rejection in this group of sensitized individuals, including T cell PRA, matching at the HLA-DR, -B , or -A loci, ischemic time, or donor age.

The Presence of Pretransplant IgG Anti-MHC Class II Antibodies is Associated with Higher Cumulative Annual Rejection Frequencies. As shown in Table 7, those patients with IgG anti-II detected at the time of transplantation had higher cumulative annual rejection frequencies than those without these antibodies (0.846 versus 0.169 high-grade rejections per patient year of followup). Among the demographic and immunologic variables examined, including the other antibody types, only pretransplant IgG anti-II was predictive of a higher cumulative annual rejection frequency, p=0.002. Neither the presence of IgG anti-I nor total T cell PRA significantly influenced the cumulative annual rejection frequencies.

Matching Between the First and Second Donor at the HLA-A Locus Predicts Early High-Grade Cellular Rejection for Recipients of a Second Cardiac Allograft Among retransplant recipients, those who received a second allograft which shared one or more HLA-A locus allotypes with the first donor had a significantly shorter time to a first high-grade cellular rejection. This difference was most notable in the first post-transplant month, where 67% of retransplant recipients of a donor #1-donor #2 HLA-A match had a high-grade cellular rejection compared with only 5% of those not receiving a heart from a second donor matched at HLA-A with the first donor (p=0.0026, odds ratio 30.0). This risk factor was independent of any anti-HLA IgG antibody effect since only ⅙ patients with donor #1-donor #2 HLA-A match had IgG anti-II pretransplant. Matching of the first and second donors at the HLA-B and DR loci did not influence the duration to early rejections among the retransplanted patients.

7.3. Discussion

In this study, we investigated the effects of anti-HLA antibodies present in two populations of sensitized individuals awaiting cardiac transplantation. IgG antibodies against non donor-specific MHC class II molecules were detected at increased frequency among both LVAD recipients and retransplant candidates. The presence of IgG antibodies against MHC class II molecules detected in recipient serum at the time of transplantation was found to be a major risk factor both for the development of early high-grade cellular rejections and for significantly increased cumulative annual rejection frequencies. These observations were independently confirmed in both populations of sensitized individuals. Neither anti-MHC class I IgG antibodies nor those detected in a conventional PRA assay were found to be predictive of earlier cellular rejections or increased cumulative annual rejection frequencies. Since both anti-HLA antibodies and early cellular rejections have been associated with accelerated graft vasculopathy in cardiac transplantation, these results emphasize the importance of specifically screening cardiac transplant candidates for the presence of IgG antibodies against MHC class II molecules, and suggest that strategies aimed at their reduction may impact on the long-term outcome of cardiac allograft recipients.

Although previous studies have identified adverse effects of anti-HLA IgG antibodies on early post-transplant graft rejection and survival, especially in instances of a positive donor-specific cross-match using unseparated donor mononuclear cells, in none of these studies was a distinction made between antibodies directed against MHC class I versus class II antigens. Acute vascular rejection and early graft failure are primarily due to preformed antibodies against MHC class I molecules, as MHC class II antigens are not expressed constitutively on graft vascular endothelium. Since 80–90% of unseparated lymphocytes are T cells, which constitutively express MHC class I but not class II molecules, a prospective cross-match using unseparated donor mononuclear cells will identify the presence in recipient sera of IgG antibodies against donor MHC class 1 antigens, but not usually donor MHC class II antigens. Because of the potential for acute vascular rejection, a positive donor-specific T cell cross-match is generally considered a contraindication for cardiac transplantation at our institution. In our study, the presence of IgG antibodies against a panel of MHC class I antigens was found to be a good predictor of those individuals who were likely to have a prolonged waiting time to cardiac transplantation, presumably due to repeated instances of positive donor-specific cross-matches which prevented cardiac transplantation.

The mechanism by which the presence of pretransplant IgG anti-II relates to the post-transplant development of earlier and more frequent high-grade cellular rejections remains conjectural at present. Recent cumulative evidence has emerged that the indirect pathway of CD4 T cell activation plays a major role in acute and chronic cardiac allograft rejection, due to continuous shedding of donor alloantigenic HLA peptides and their processing by host antigen presenting cells (APCs) such as macrophages and B cells. In previous studies, we have shown that acute cardiac cellular rejection is accompanied by the appearance both in the circulation and in the allograft of recipient T cells reactive with donor HLA-DR peptides presented by self-APCs. Primary rejections appear to be invariably accompanied by indirect recognition of a dominant HLA-DR allopeptide, whereas recurrent rejections appear to be accompanied by intermolecular spreading and T cell recognition of multiple donor HLA-DR alloantigenic determinants[17]. Similar patterns of progressive intra- and intermolecular HLA-DR epitope spreading can be detected in cardiac transplant recipients developing accelerated transplant-related coronary artery disease. This diversification of the immune response has been postulated to be a result of activation of antigen-specific B cells by soluble HLA-DR molecules, and the subsequent efficient presentation of multiple HLA-DR allopeptides by self B cells to CD4 T cells. Therefore, the relationship between recurrent high-grade cellular rejections and pre-existing IgG anti-MHC class II antibodies documented in this study may in fact indirectly reflect the presence in sensitized cardiac transplantation candidates of circulating memory B cells with reactivity to allogeneic HLA-DR molecules. The presence of alloreactive B cells in sensitized candidates may reflect either exposure to alloantigens following administration of blood products, pregnancy or prior transplantation, or induction of an autoimmune process in immunogenetically susceptible LVAD recipients.

Following activation of CD4 helper T cells by allogeneic HLA-DR peptides presented by self APCs, IL-2 elaboration by these cells leads to amplification of the CD8 cytotoxic response to donor MHC class I alloantigens, resulting in fulminant cellular rejection of the organ. In the present study, we additionally found that a major risk factor for early high-grade cellular rejection of the second allograft in retransplant patients was a match at the HLA-A MHC class I locus between the first and second donors. The fact that only one of six patients with a donor #1-donor #2 match also had IgG anti-II indicates that matching between donors at the HLA-A locus is a very strong, independent risk factor for high-grade cellular rejection post-transplant, and suggests that memory CD8 T cell clones present in the recipient could respond rapidly to the shared HLA-A antigen on the endothelium of the second allograft without requiring initial help from CD4 T cells. In the absence of a prominent CD8 memory response to HLA-A antigens, fulminant cellular rejection appears to require the amplification pathways triggered by activation of alloreactive B cells, and indirectly measured by circulating IgG anti-II.

Since the presence of IgG anti-MHC class I or II antibodies in sensitized patients leads to a prolonged waiting time for transplantation, early post-transplant humoral rejection, and earlier and more frequent post-transplant cellular rejections, strategies to reduce the levels of these antibodies prior to transplantation are needed for this rapidly enlarging pool of patients awaiting cardiac transplantation. Prior experience with sensitized patients has focused on immunosuppressive therapies initiated after transplantation, including plasmapharesis and photophoresis, to avoid the negative consequences of these pretransplant antibodies. We emphasize the need to carefully screen all patients at risk for sensitization prior to transplantation, and to identify the presence, isotype and specificity of anti-HLA antibodies which portend heightened risk for adverse post-transplant outcomes. We advocate institution of immunosuppressive strategies in these patients prior transplantation. These strategies will need to be tailored to the antibody specificity detected in any given patient and the clinical complication it portends. Such strategies might include the use of intravenous immunoglobulin (IVIg), plasmapharesis with B cell immunosuppression or Protein A column immunoadsorption. In view of the increasing use of LVAD support, and the growing numbers of patients awaiting retransplantation, high priority should be given to evaluation of therapeutic protocols aimed at reducing anti-HLA antibodies prior to cardiac transplantation.

Various publications are cited herein which are hereby incorporated by reference in their entireties.

TABLE 1

Influence of high cumulative annual rejection frequency on development of transplant-related coronary artery disease (TCAD)*

| post-transplant interval (years) | <0.75 rejections/year | % probability of develoning TCAD >0.75 rejections/year |
|---|---|---|
| 1 | 9 | 20 |
| 2 | 34 | 55 |
| 3 | 45 | 94 |
| 4 | 55 | 94 |

*P = 0.0002 (Kaplan-Meier log rank statistics)

TABLE 2

A positive lymphocyte growth assay (LGA) predicts progression of a low-grade biopsy to high-grade cellular rejection in recipients of cardiac transplantation.
Probability of a High-Grade Rejection Within 90 Days

|  | Pos. LGA (Score > 0) | Neg. LGA (Score = 0) | p value | odds ratio |
|---|---|---|---|---|
| No. HLA-DR Matches | .64 | .40 | 0.0002 | 2.73 |
| 1 or 2 HLA-DR Matches | .58 | .21 | <0.0001 | 5.22 |

TABLE 3

The presence of IgG antibodies against MHC class II molecules (IgG anti-II) predicts progression of a low-grade biopsy to high-grade cellular rejection in cardiac transplantation patients with complete donor-recipient mismatches at the HLA-DR locus.
Probability of a High-Grade Rejection Within 90 Days

| Anti-HLA Antibody | No. HLA-DR Matches | | | | 1 or 2 HLA-DR Matches | | | |
|---|---|---|---|---|---|---|---|---|
| IgG anti-H | .42 | .66 | <.01 | 2.68 | .27 | .29 | .85 | 1.08 |
| IgG anti-I | .43 | .60 | .01 | 1.92 | .26 | .31 | .41 | 1.31 |
| IgG anti-I (anti-II) | .34 | .31 | .42 | .83 | | | | |

TABLE 3-continued

The presence of IgG antibodies against MHC class II molecules (IgG anti-II) predicts progression of a low-grade biopsy to high-grade cellular rejection in cardiac transplantation patients with complete donor-recipient mismatches at the HLA-DR locus.
Probability of a High-Grade Rejection Within 90 Days

| Anti-HLA Antibody | No. HLA-DR Matches | | | | 1 or 2 HLA-DR Matches | | | |
|---|---|---|---|---|---|---|---|---|
| IgM anti-II | .51 | .44 | .32 | .75 | .30 | .28 | .77 | .90 |
| IgM anti-I | .50 | .43 | .33 | .73 | .30 | .29 | .90 | .95 |

TABLE 4

Multivariable equation describing the patient incremental factors associated with 90-day progression from a low-grade biopsy to a high grade rejection during the first year post cardiac transplantations.

| | Odds ratio | 95% CI | p value |
|---|---|---|---|
| positive LGA | 4.34 | 1.73, 10.91 | 0.0018 |
| positive IgG anti-II | 2.22 | 1.00, 5.02 | 0.0561 |
| full DR mismatch | 1.89 | 0.85, 4.27 | 0.1211 |

TABLE 5

In Comparison to NYHA Class IV Controls Awaiting Cardiac Transplantation, the Frequency of Anti-MHC Class II Antibodies is Increased in Both LVAD Recipients and Retransplant (ReTx) Candidates, Whereas the Frequencies of Anti-MHC Class I Antibodies and Total T Cell PRA Are Increased in LVAD Recipients Only.*

| | NYHA Class IV (n = 66) n (%) | LVAD (n = 45) n (%) | odds ratio | ReTx (n = 23) n (%) | odds ratio |
|---|---|---|---|---|---|
| T Cell PRA | 9 (13) | 29 (64)* | 11.6 | 5 (22) | |
| IgG Anti-I | 2 (3) | 19 (43)* | 25.6 | 1 (6) | |
| IgG Anti-II | 2 (3) | 15 (33)* | 15.5 | 7 (29)* | 14.0 |

*p < 0.0001

TABLE 6

By multivariable analysis, using the Cox Proportional Hazards model, pretransplant IgG anti-II, and to a lesser extent IgG anti-I, is predictive of earlier first high-grade cellular rejection after cardiac transplantation in highly sensitized individuals (n = 68).

| Variable | coefficient +/− SE | p value | Risk ratio | 95% CI |
|---|---|---|---|---|
| IgG anti-II | 1.035 +/− 0.4393 | 0.0184 | 2.816 | (1.19, 6.66) |
| IgG anti-I | 0.908 +/− 0.5295 | 0.0863 | 2.480 | (0.88, 7.00) |

TABLE 7

Influence of pretransplant anti-HLA antibodies in sensitized patients (n = 68) on cumulative annual rejection frequencies of a subsequent cardiac transplant.*
Cumulative Annual Rejection Frequency
(No. of 3A or 3B rejections/yr)

| | Positive | Negative | p value |
|---|---|---|---|
| IgG anti-II | 0.846 | 0.169 | 0.002 |
| IgG anti-I | 0.611 | 0.291 | 0.09 |
| T Cell PRA | 0.468 | 0.328 | 0.88 |

What is claimed is:

1. A method for assessing the risk of transplantation rejection in a recipient host comprising the following steps:
 (a) determining the HLA-DR of the recipient and the HLA-DR of a donor and determining if the recipient and donor are DR mismatched;
 (b) assaying for the presence of activated T-lymphocytes in the recipient;
 (c) assaying for the presence of circulating IgG anti-HLA Class II antibodies in the serum of the recipient;
 wherein the presence of activated T-lymphocytes in the recipient and the presence of circulating IgG anti-HLA Class II antibodies in a DR mismatched recipient indicates a high risk of transplantation rejection.

2. The method of claim 1 wherein the recipient host has received a tissue allograft.

3. The method of claim 1 wherein the recipient host has received a heart transplant.

4. The method of claim 1 wherein the HLA-DR of the recipient is determined using a microcytotoxicity assay.

5. The method of claim 1 wherein the HLA-DR of the recipient is determined using a mixed lymphocyte reaction.

6. The method of claim 1 wherein the HLA-DR of the recipient is determined using a polymerase chain reaction.

7. The method of claim 1 wherein the presence of activated lymphocytes is measured using a lymphocyte growth assay.

8. A method for predicting whether or not a subject who has received a tissue allograft is likely to reject the tissue allograft comprising detecting IgG anti-HLA DR antibodies in serum from the subject by determining reactivity of the serum with panels of separated B- and T-lymphocytes from control individuals representative of the most frequently encountered HLA class I and class II antigens and obtaining a ratio of reactivity with B-versus T-lymphocytes, wherein detection of greater reactivity with B-lymphocytes relative to reactivity with T-lymphocytes indicates that such antibodies are present and indicates that the tissue allograft recipient is likely to reject the tissue allograft.

* * * * *